United States Patent
Kleinberg et al.

(10) Patent No.: US 9,579,364 B2
(45) Date of Patent: Feb. 28, 2017

(54) METHODS FOR TREATING BENIGN PROSTATIC HYPERTROPHY (BPH)

(71) Applicants: David L. Kleinberg, New York, NY (US); Sergio Vidal, Vigo (ES); Weifeng Ruan, Forest Hills, NY (US)

(72) Inventors: David L. Kleinberg, New York, NY (US); Sergio Vidal, Vigo (ES); Weifeng Ruan, Forest Hills, NY (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 14/299,596

(22) Filed: Jun. 9, 2014

(65) Prior Publication Data

US 2014/0349937 A1    Nov. 27, 2014

Related U.S. Application Data

(63) Continuation-in-part of application No. 13/852,114, filed on Mar. 28, 2013, which is a continuation-in-part of application No. 10/502,364, filed as application No. PCT/US03/01886 on Jan. 22, 2003, now abandoned.

(60) Provisional application No. 61/616,729, filed on Mar. 28, 2012, provisional application No. 60/351,307, filed on Jan. 22, 2002.

(51) Int. Cl.
| | |
|---|---|
| A61K 38/31 | (2006.01) |
| A61K 31/4706 | (2006.01) |
| A61K 31/47 | (2006.01) |
| A61K 31/7088 | (2006.01) |
| A61K 31/7105 | (2006.01) |
| A61K 38/27 | (2006.01) |

(52) U.S. Cl.
CPC .............. *A61K 38/31* (2013.01); *A61K 31/47* (2013.01); *A61K 31/4706* (2013.01); *A61K 31/7088* (2013.01); *A61K 31/7105* (2013.01); *A61K 38/27* (2013.01)

(58) Field of Classification Search
None
See application file for complete search history.

(56) References Cited

U.S. PATENT DOCUMENTS

| | | |
|---|---|---|
| 5,350,836 A | 9/1994 | Kopchick et al. |
| 6,274,562 B1 | 8/2001 | Baserga et al. |
| 6,331,526 B1 | 12/2001 | Baserga et al. |
| 6,448,086 B1 | 9/2002 | Khosravi et al. |
| 7,432,244 B2 | 10/2008 | Deshayes et al. ............ 514/1.1 |
| 2004/0115209 A1 | 6/2004 | Saragovi et al. .......... 424/178.1 |
| 2011/0034381 A1 | 2/2011 | Kleinberg et al. |
| 2012/0302505 A1* | 11/2012 | Fetzer ................ A61K 47/4823 514/15.4 |
| 2013/0261057 A1 | 10/2013 | Kleinberg ................. 514/11.1 |
| 2014/0349937 A1 | 11/2014 | Kleinberg et al. ........... 514/11.1 |

FOREIGN PATENT DOCUMENTS

| | | |
|---|---|---|
| DE | 3726517 | 3/1988 |
| WO | 0006185 | 2/2000 |
| WO | WO0006185 | 2/2000 |
| WO | 03061592 | 7/2003 |

OTHER PUBLICATIONS

Bruns et al., "SOM230: a novel somatostatin peptidomimetic with broad somatotropin release inhibiting factor (SRIF) receptor binding and a unique antisecretory profile", European Journal of Endocrinology, 2002, 146:707-716.
Ruan et al, "SOM230 inhibits insulin-like growth factor-I action in mammary gland development by pituitary independent mechanism: mediated through somatostatin subtype receptor 3?", Molecular Endocrinology, 2006, 20:(2):426-436.
U.S. Appl. No. 14/299,596, filed Jun. 9, 2014.
Chung et al., "Tissue interactions and prostatic growth. I. Induction of adult mouse prostatic hyperplasia by fetal urogenital sinus implants", Biology of Reproduction, 1984, vol. 31, pp. 155-163.
Chung et al., "Tissue interactions and prostatic growth: A new mouse model for prostatic hyperplasia", Annals New York Academy of Sciences, 1984, vol. 438, pp. 394-404.
Chung et al., "Characterization of fetal urogenital sinus-induced prostatic hyperplasia in the mouse: Time course, hormonal requirement, age dependency, and responsiveness of various adult organs to growth induction by fetal urogenital sinus tissues", Biology of Reproduction, 1988, vol. 39, pp. 50-57.
Marengo et al., "An orthotopic model for the study of growth factors in the ventral prostate of the rat: Effects of epidermal growth factor and basic fibroblast growth factor", Journal of Andrology, 1994, vol. 15, No. 4, pp. 277-286.
Miller et al., "Tissue interactions and prostatic growth. II. Morphological and biochemical characterization of adult mouse prostatic hyperplasia induced by fetal urogenital sinus implants", The Prostate, 1985, vol. 6, pp. 241-253.
Sikes et al., "Inhibition of experimentally induced mouse prostatic hyperplasia by castration or steroid antagonist administration", Biology of Reproduction, 1990, vol. 43, pp. 353-362.
Scolnik et al., "Comparative study of experimentally induced benign and atypical hyperplasia in the ventral prostate of different rat strains", Journal of Andrology, 1994, vol. 15, No. 4, pp. 287-297.
Kleinberg et al., "Insulin-like growth factor (IGF)-I controls prostate fibromuscular development: IGF-I inhibition prrevents both fibromuscular and glandular development in eugonadal mice", Endocrinology, 2007, 148, 1080-1088.
Cunningham et al., "Clinical manifestations and diagnosis of benign prostatic hyperplasia", 2011, UpToDate http://www.uptodate.com/contents/clinical-manifestations-and-diagnosis-of-benign-prostatic-hyperplasia, Version 19.2, 1-12.
Kopchick et al., "Growth hormone receptor antagonists: discovery, development, and use in patients with acromegaly", Endocrine Reviews, 2002, 23, 623-646.

(Continued)

*Primary Examiner* — Maury Audet
(74) *Attorney, Agent, or Firm* — Klauber & Jackson LLC

(57) ABSTRACT

Therapeutic methods for treating a subject with benign prostatic hypertrophy by inhibition of the activity of insulin-like growth factor-I (IGF-I) to reduce the amount of prostatic hyperplastic tissue in the subject are described herein.

15 Claims, 5 Drawing Sheets

(56) References Cited

OTHER PUBLICATIONS

Lee et al., "Enhancement of insulin-like growth factor signaling in human breast cancer: estrogen regulation of insulin receptor substatrate-1 expression in vitro and in vivo", Molecular Endocrinology, 1999, 13, 787-796.
Ruan et al., "Evidence that insulin-like growth factor I and growth hormone are rquired for prostate gland development", Endocrinology, 1999, 140, 1984-1989.
Plonowski et al., "Inhibition of proliferation of PC-3 human prostate cancer by antagonists of growth hormone-releasing hormone: lack of correlation with the levels of serum IGF-I and expression of tumoral IGF-II and vascular endothelial growth factor", The Prostate, 2002, 52, 173-182.
Rose et al., "Growth hormone receptor antagonist improves insulin resistance in acromegaly", Growth Hormone & IGF Research, 2002, 12, 418-424.
Drake, "Experience with pegvisomant in the treatment of acromegaly", Growth Hormone & IGF Research Supplement A, 2001, S111-S114.
Drake et al., "Clinical use of a growth hormone receptor antagonists in the treatment of acromegaly", Trends in Endocrinology & Metabolism, 2001, 12, 408-413.
Fujii et al., "Somatostatin receptor subtype SSTR2 mediates the inhibition of high-voltage-activated calcium channels by somatostatin and its analogue SMS 201 995", FEBS Letters, 1994 pp. 117-120 vol. 355.
Hesse et al., "Role of somatostatin-14 and its analogues in the management of gastrointestinal fistulae: clinical data", Gut, 2002, pp. iv11-iv20, vol. 49 (Supp. IV).
Parrizas et al., "Specific inhibition of insulin-like growth factor-1 and insulin receptor tyrosine kinase activity and biological function by tyrphostins", Endocrinology, 1997, pp. 1427-1433, vol. 138, No. 4.
Pietrzkowski et al., "Inhibition of cellular proliferation by peptide analogues of insulin-like growth factor 1", Cancer Research, 1992, pp. 6447-6451, vol. 52.
Pietrzkowski et al., "Inhibition of growth of prostatic cancer cell lines by peptide analogues of insulin-like growth factor 1", Cancer Research, 1993, pp. 1102-1106, vol. 53.
Robinette, "Sex-hormone-induced inflammation and fibromuscular proliferation in the rat lateral prostate", The Prostate, 1988, pp. 271-286, vol. 12.
Couse et al., "Estrogen receptor null mice: What have we learned and where will they lead us?", Endocrine Reviews, 1999, vol. 20, pp. 358-417.
Gharib et al., "Molecular biology of the pituitary gonadotropins", Endocrine Reviews, 1990, vol. 11, pp. 177-199.
Lundgren et al., "Treatment of prostatitis in the rat", The Prostate, 1984, vol. 5, pp. 277-284.
Naslund et al., "The role of androgens and estrogens in the pathogenesis of experimental nonbacterial prostatitis", J Urol, 1988, vol. 140, pp. 1049-1053, Abstract only.
Piacsek et al., "Effects of castration and gonadal hormones on hypothalamic conent of luteinizing hormone releasing factor (LRF)", Endocrinology, 1966, 79, 432-439.
Hieble et al., "Animal models for benign prostatic hyperplasia", Handbook of Experimental Pharmacology, 2011, 202, 69-79.
Mahapokai et al., "Models for studying benign prostatic hyperplasia", Prostate Cancer and Prostatic Diseases, 2000, 3, 28-33.

Colao et al., "Prostatic hyperplasia: an unknown feature of acromegaly", Journal of Clinical Endocrinology & Metabolism, 1998, 83, 775-779.
Gable et al., Mol Cancer Ther, 5:1079-1086, 2006.
Piacsek et al., "Effects of castration and gonadal hormones on hypothalamic content of luteinizing hormone releasing factor (LRF)", Endocrinology, 1966, vol. 79, pp. 432-439.
Hieble, Handbood of Experimental Pharmacology, 202:69-79, 2011.
Mahapokai et al., Prostate Cancer and Prostatic Diseases, 3:28-33, 2000.
Ruan et al., Endocrinology, 140(5):1984-1989, 1999.
Fuji et al., "Somatostatin receptor subtype SSTR2 mediates the inhibition of high-voltage-activated calcium channels by somatostatin and its analogue SMS 201-995", FEBS Letters, 1994, pp. 117-120, vol. 355.
Kleinberg DL et al. Insulin-like growth factor (IGF)-I controls prostate fibromuscular development: IGF-I inhibition prevents both fibromuscular and glandular development in eugonadal mice, Endocrinology 148:1080-1088 (2007).
Cunningham GR et al. Clinical manifestations and diagnosis of benign prostatic hyperplasia, UpToDate pp. 1-12 (2011).
Kopchick JJ et al. Growth hormone receptor antagonists: discovery, development, and use in patients with acromegaly, Endocrine Reviews 23(5):623-646 (2002).
Lee, AV et al. Enhancement of insulin-like growth factor signaling in human breast cancer: estrogen regulation of insulin receptor substrate-1 expression in vitro and in vivo, Molecular Endocrinology 13:787-796 (1999).
Ruan, W et al. Evidence that insulin-like growth factor I and growth hormone are required for prostate gland development, Endocrinology 140:1984-1989 (1999).
Plonowski, A et al. Inhibition of proliferation of PC-3 human prostate cancer by antagonists of growth hormone-releasing hormone: lack of correlation with the levels of serum IGF-I and expression of tumoral IGF-II and vascular endothelial growth factor, The Prostate 52:173-182 (2002).
Rose, DR et al. Growth hormone receptor antagonist improves insulin resistance in acromegaly, Growth Hormone & IGF Research 12:418-424 (2002).
Drake, WM Experience with pegvisomant in the treatment of acromegaly, Growth Hormone & IGF Research Supplement A: S111-S114 (2001).
Drake, WM et al. Clinical use of a growth hormone receptor antagonist in the treatment of acromegaly, Trends in Endocrinology & Metabolism 12(9):408-413 (2001).
Colao et al., Journal of Clinical Endocrinology & Metabolism, 83:775-779, 1998.
Shimon et al., "PTR-3173 (SomatoprimTM), a novel somatostatin analog with affinity for somatostatin receptors 2, 4 and 5 is a potent inhibitor of human GH secretion", J. Endocrinol. Invest., 2004, 27: 721-727.
Afargan et al., "Novel Long-Acting Somatostatin Analog with Endocrine Selectivity: Potent Suppression of Growth Hormone But Not of Insulin", Endocrinology, 2001, 142:477-486.
Kim et al., "Preventive Effects of Oligomerized Polyphenol on Estradiol-Induced Prostatitis in Rats", Yonsei Med J, 2009, 50:391-398.

* cited by examiner

METHODS FOR TREATING BENIGN PROSTATIC HYPERTROPHY (BPH)

CROSS REFERENCE TO RELATED APPLICATIONS

This application is a Continuation in Part of co-pending U.S. application Ser. No. 13/852,114, filed Mar. 28, 2013, which in turn claims priority from U.S. Provisional Application Ser. No. 61/616,729, filed Mar. 28, 2012, and is a Continuation in Part of co-pending U.S. application Ser. No. 10/502,364, filed Jun. 1, 2006, which is a National Stage Application claiming priority from PCT/US03/01886, filed Jan. 22, 2003, which in turn claims priority from U.S. Provisional Application Ser. No. 60/351,307, filed Jan. 22, 2002. Applicants claim the benefits of 35 U.S.C. §120 as to the United States Utility applications and the PCT application and priority under 35 U.S.C. §119 as to the United States Provisional applications, each of which applications is specifically incorporated herein by reference in its entirety.

FIELD OF INVENTION

The present invention relates to therapeutic methods for treating benign prostatic hypertrophy by inhibition of the activity of insulin-like growth factor-I (IGF-I). Methods encompass the use of IGF-I inhibitors that act directly on IGF-I, as well as the use of compounds that lower the effective level of IGF-I, or interfere with post receptor effects of IGF-I action in the prostate.

BACKGROUND OF THE INVENTION

Little is known about the hormonal control of prostate development. Previously, it was assumed that the development of the prostate was controlled primarily by testosterone. Recently, both insulin growth factor-I (IGF-I) and testosterone (T) were shown to be essential for development of the prostate gland, with the hormones working additively and/or synergistically, but also having independent effects (Ruan et al. (1999) Endocrinology 140:1984-1989).

The term "benign prostatic hyperplasia" ("BPH") is generally used to represent clinical enlargement of the prostate or lower urinary tract symptoms including irritative or obstructive voiding pattern, urinary retention, and frequent urination with an increased residual urine volume. Benign prostatic hypertrophy is reported to occur in over 80% of the male population before the age of 80 years, and that as many as 25% of men reaching age 80 years will require some form of treatment, usually in the form of a surgical procedure (Partin (2000) Benign Prostatic Hyperplasia, in *Prostatic Diseases* (Lepor H. ed.), W.B. Saunders, Philadelphia, pp 95-105). While the cause has remained obscure, it is generally recognized that the two most important factors necessary for the induction of BPH are the presence of the testes and aging.

Several possible etiologies have been suggested as causing BPH, including testosterone, or a relative reduction in testosterone with an increase in estrogen. Treatment with 5α-reductase inhibitors, which reduce conversion of testosterone to dihydrotestosterone (the more active androgen for prostate growth), has been found to be only minimally effective in most patients. The adrenergic receptor antagonist, terazosin (Hytrin™) has been used to help symptoms of urinary obstruction caused by increased smooth muscle tone, but is found to be only temporarily effective and is associated with cardiovascular side-effects.

The role of excess GH and IGF-I on development of BPH and/or prostatic carcinoma was studied in patients suffering from acromegaly, a pituitary disorder caused in most cases by a GH-secreting adenoma (Colao et al. (1998) J. Clin. Endocrinol. Metab. 83:775-779). Compared to healthy subjects, a significant increase in transversal prostatic diameter and volume was observed in acromegalics. Colao et al. further disclose that symptoms due to prostatic, seminal vesicle, and/or urethral disorders or obstruction were not experienced by acromegalics. Treatment with octreotide for 1 year induced normalization of circulating GH and IGF-I levels in most of the patients treated, as well as a reduction in prostate volume.

In light of the above, there is a need for a method for treating BPH that inhibits, prevents or reverses the progression of the disorder such that the need for surgical treatment is delayed or prevented.

SUMMARY OF THE INVENTION

This invention rests in part on the discovery that IGF-I stimulates fibromuscular hyperplasia in the prostate, while testosterone increases intraluminal epithelial glandular development. Prior studies have underscored the importance of the relationship between the stromal and glandular elements in prostate development (Cunha (1973) Anat. Rec. 175:87-96) (Norman et al. (1986) Prostate, 8:209-220), as well as the role of the basal cell in BPH. Indeed, it is understood that BPH is associated with hyperplasia of both fibromuscular and glandular compartments of the prostate. Fibromuscular hyperplasia, particularly in the periurethral portion of the prostate, appears to be responsible for many of the symptoms of BPH. Symptomatic BPH is characterized by lower urinary tract symptoms including irritative or obstructive voiding pattern, urinary retention, and/or frequent urination with an increased residual urine volume.

Prior investigations have concluded that a number of hormones, including IGF-I, may play a role in development of glandular structures of the prostate and/or development of prostate cancer. The results described herein provide the first direct evidence that out of a number of hormones that affect the prostate, IGF-I specifically induces fibromuscular hyperplasia of the prostate.

Accordingly, in a first aspect, the present invention provides a method for treating benign prostatic hypertrophy (BPH), comprising administering a therapeutically effective amount of an inhibitor of insulin-like growth factor-I (IGF-I) activity to a patient in need thereof. In one embodiment of the therapeutic method of the invention, the inhibitor is Somatostatin-14 or an analog thereof, such as, for example, SOM230. In another embodiment, the inhibitor is a growth hormone (GH) antagonist, for example, pegvisomant (Somavert™). In a further embodiment, the inhibitor of IGF-I is an antibody, particularly a blocking or neutralizing antibody to IGF-I, for example, αIR-3. In another embodiment, the inhibitor of IGF-I is an insulin-like growth factor binding protein, including for example IGFBP1 (Yee et al, (2000) Proc. Am. Soc. Clin. Oncol. Annual Meeting, Abstract 813) or IGFBP5. See also U.S. Pat. No. 7,432,244. In a further embodiment, the inhibitor of IGF-I interferes with post receptor effects of IGF-I action in the prostate, including but not limited to blocking or affecting the intracellular signaling pathway. In one embodiment, the IGF-I inhibitor blocks the activity of downstream signaling molecules of IGF, including but not limited to insulin receptor substrate (for example IRS-1 and/or IRS-2). In another embodiment, the inhibitor of IGF-I activity is an agent that lowers GH production or levels, for example, octreotide (Sandostatin™ or Sandostatin LAR™; Novartis) or lanreotide (Ipsen Beaufour Biomeasure). In another embodiment, the inhibitor of IGF-I activity is an agent which decreases the rate of IGF-I synthesis. In another embodiment, the inhibitor is an agent which increases the rate of IGF-I degradation or clearance.

In a particular embodiment, the present invention provides a method for treating BPH, comprising administering a therapeutically effective amount of a somatostatin analog to a patient in need thereof. As indicated in greater detail herein below, somatostatin analogs act as inhibitors of insulin-like growth factor-I (IGF-I) activity. The somatostatins, for example, act as regulators of exocrine and endocrine secretion and affect the release of a plurality of hormones, including IGF-I via indirect means. Somatostatin-14 (SS-14 or SST-14), for example, was originally isolated from ovine hypothalamic extracts based on its ability to inhibit the secretion of growth hormone by primary cultures of enzymatically dispersed rat anterior pituitary cells. SS-14 is a small cyclic neuropeptide hormone that exhibits broad inhibitory effects on endocrine secretions including the production of growth hormone (GH), glucagon, and insulin. SS-14 binds somatostatin receptor subtypes (SSTRs) 1-5. It is, therefore, viewed as a universal SSTR ligand. The structure of somatostatin-14 (SS-14) is as follows:

The somatostatin analog SOM230 is an exemplary compound envisioned for use in the present methods. SOM230, also known as pasireotide, is a cyclohexapeptide engineered to bind to multiple somatostatin receptor subtypes (i.e., 1, 2, 3, and 5). It has been characterized as a potent and selective octapeptide analog of somatostatin with prolonged action. Accordingly, it mimics the action of natural somatostatin. See, for example, Bruns et al. 2002, Eur J Endocrin 146:707, the entire content of which is incorporated herein in its entirety. SOM230 has, moreover, been shown to prevent mammary development in rats via two mechanisms (Ruan, W et al (2006) Mol Endocrinology 20 (2):426-436). One of them is an inhibitory effect on growth hormone secretion from the pituitary which can cause reduction of serum IGF-I. The other is a direct inhibition of IGF-I action in the mammary gland as demonstrated by a reduction in IRS-1 phosphorylation in the mammary gland. It has been postulated that this effect of SOM230 is mediated by either somatostatin receptor subtype (SSTR) 3 or 5 and that this causes an increase in IGF binding protein 5 (IGFBP5) which in turn blocks the local action of IGF-I in the mammary gland (Ruan, W et al (2006) Mol Endocrinology 20(2):426-436). Somatostatin analog SOM 230 is the subject of U.S. Pat. No. 7,473,761 of Novartis (having a foreign priority date of Aug. 1, 2000). U.S. Pat. No. 7,473,761 describes SOM230, compositions thereof, and methods for preventing or treating disorders with an etiology comprising or associated with excess GH-secretion and/or excess IGF-I.

The structure of SOM230 is as follows:

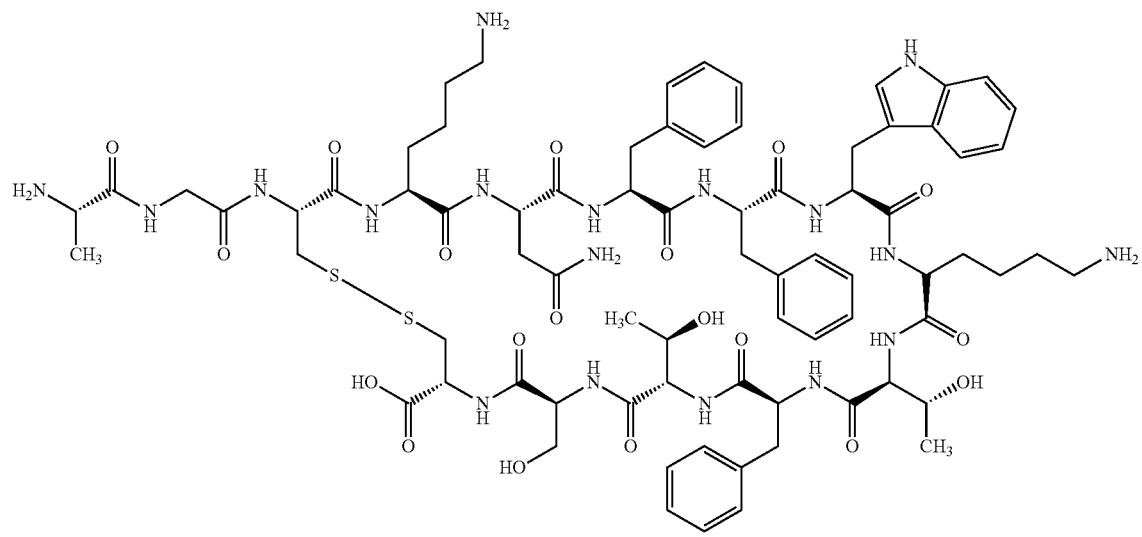

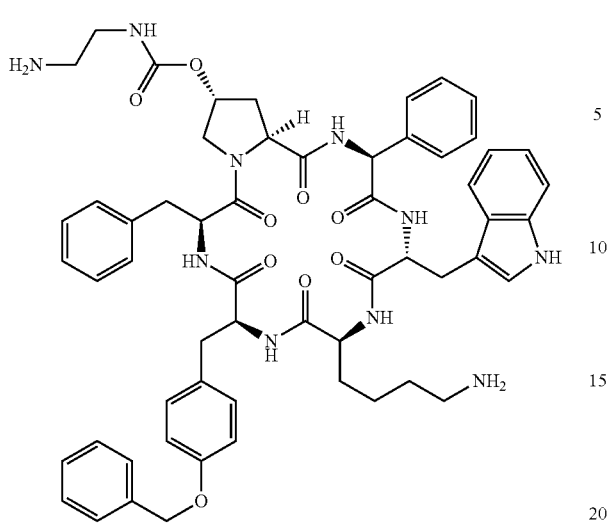

Other somatostatin analogs and/or other compounds which bind or otherwise associate with and activate/engage the SSTR3 and/or SSTR5 receptors are suitable for use in the invention. The action of a somastostatin analog and its ability or capability to bind to or otherwise associate with SSTR3 and/or SSTR5 somatostatin receptor(s) can be determined by the skilled artisan using routine protocols and/or those disclosed herein. Additional somatostatin analogs include but are not limited to BIM23A779 (Neuroendocrinology 83:258-263, 2006), AN-238 (Clin Cancer Research 7:2854-2861, 2001) (2-pyrrolinodoxorubicin (AN-201) linked to octapeptide carrier RC-121) (Nagy A et al (1998) Proc Natl Acad Sci USA 95:1794-1799), RC-121 (D-Phe-Cys-Tyr-D-Trp-Lys-Val-Cys-Thr-NH$_2$) (Cai, R-Z et al (1986) Proc Natl Acad Sci USA 83:1896-1900), cyclic somatostatin analog peptide which selectively binds to the SRIF receptor SSTR3 (described in U.S. Pat. No. 6,579, 967), and Somatostatin Tumor Inhibiting Analog (Anaspec). Nikiforovich has, moreover, used molecular modeling of constrained somatostatin analog peptides to probe SSTR specificity (Nikiforovich G V et al (2007) Chemical Biology and Drug Design 69(3):163-169). These studies serve as templates for design of conformationally-constrained non-peptide scaffolds that interact with specific SSTR subtypes.

The structure of AN-238, which includes RC-121, is as follows:

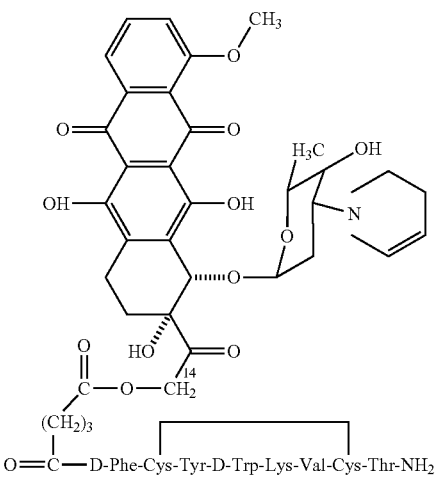

The structure of RC-121 is as follows:

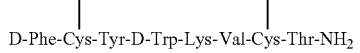

Also envisioned herein for use in the present methods is KE108, a nonapeptide somatostatin analog with a reduced size and stabilized structure. KE108 exhibits extremely high affinity for all five somatostatin receptor subtypes and is stable for several hours in human serum. See, for example, Reubi et al. (2002, European Journal of Pharmacology 456:45-49), the entire contents of which is incorporated herein by reference.

The structure of KE108 is as follows:

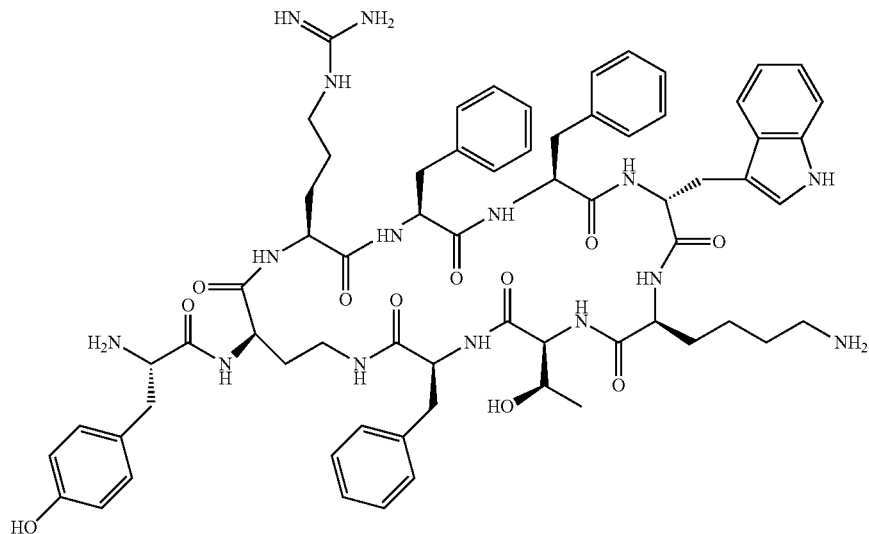

KE108

Also envisioned herein for use in the present methods is a small molecule IGF-I receptor kinase specific inhibitor. The diaryl urea compound PQ401, for example, was identified in a chemical library screen as a potent inhibitor of IGF-IR signaling (Gable et al., Mol Cancer Ther 2006, 5:1079-1086; the entire content of which is incorporated herein by reference). Other compounds within this class of compounds are, furthermore, envisioned herein. Given its advantageous properties, PQ401 is an exemplary small molecule IGF-I receptor kinase specific inhibitor envisioned for use in the present methods.

The structure of PQ401 is as follows:

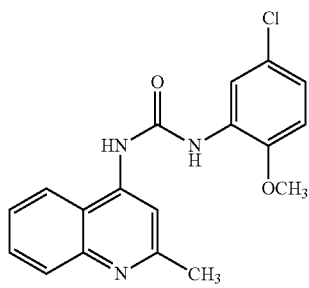 [SMILES: COc1ccc(Cl)cc1NC(=O)Nc1cc(C)nc2ccccc12]

Other exemplary agents/compounds which may be utilized in methods described herein include the IGFBP family of proteins. IGFBPs are described in, for example, U.S. Pat. No. 7,432,244 and U.S. Provisional Application 60/275,904, as well as Jones and Clemmons (1995, Endocr Rev 16:3-34), Bach And Rechler (1995, Diabetes Reviews 3:38-61), and Clemmons et al. (1993, Annal NY Acad Sci, USA 692:10-21), the entire content of each of which is incorporated herein in its entirety. Nucleic and amino acid sequences of human, mouse, and rat IGFBP1 are available via NCBI Reference Sequence Nos. NM_000596.2, NM_008341.4, and NM_013144.1, respectively. Nucleic and amino acid sequences of human, mouse, and rat IGFBP5 are available via NCBI Reference Sequence Nos. NM_000599.3 and GenBank No. CR456809.1 9 (both human), NM_010518.2, and NM_012817.1, respectively.

In accordance with the above, a method for treating benign prostatic hyperplasia (BPH) disease is presented, the method comprising administering a therapeutically effective amount of an inhibitor of IGF-I activity to a patient with BPH, wherein the therapeutically effective amount of the inhibitor of IGF-I activity is administered to reduce the amount of prostatic hyperplastic tissue in the patient and thereby alleviate undesirable symptoms of BPH in the patient. In a particular embodiment thereof, the inhibitor of IGF-I activity is somatostatin 14, a somatostatin analog, or a small molecule IGF-I receptor kinase specific inhibitor. In a more particular embodiment thereof, the somatostatin analog is selected from SOM230, BIM23A779, KE108, AN-238, and RC-121. As described herein, the small molecule IGF-I receptor kinase specific inhibitor may be PQ401. As further described herein the methods alleviate or reduce undesirable symptoms of BPH in the patient such as irritative or obstructive voiding pattern, urinary retention, and/or frequent urination with an increased residual urine volume. In an embodiment thereof, the therapeutically effective amount of the inhibitor of IGF-I activity is administered via a pharmaceutical composition comprising the therapeutically effective amount of the inhibitor of IGF-I activity and a pharmaceutically acceptable carrier. In another embodiment, the pharmaceutical composition consists essentially of the therapeutically effective amount of an inhibitor of IGF-I activity. In a more particular embodiment, the subject is a human.

In another aspect, a method for treating benign prostatic hyperplasia (BPH) disease is described, the method comprising administering a pharmaceutical composition comprising or consisting essentially of a therapeutically effective amount of an inhibitor of IGF-I activity and a pharmaceutically acceptable carrier/excipient to a patient with BPH, wherein the pharmaceutical composition is administered to reduce the amount of prostatic hyperplastic tissue in the patient and thereby alleviate adverse symptoms of BPH in the patient, wherein the adverse symptoms comprise irritative or obstructive voiding pattern, urinary retention, or frequent urination with an increased residual urine volume. In a particular embodiment, the inhibitor of IGF-I activity is somatostatin 14, a somatostatin analog, or a small molecule IGF-I receptor kinase specific inhibitor. In a more particular embodiment, the somatostatin analog is selected from SOM230, BIM23A779, KE108, AN-238, and RC-121. As described herein, the small molecule IGF-I receptor kinase specific inhibitor may be PQ401. In another embodiment, the pharmaceutical composition consists essentially of the therapeutically effective amount of an inhibitor of IGF-I activity. In a more particular embodiment, the subject is a human.

In a further aspect, a method for treating benign prostatic hyperplasia (BPH) disease in a patient to delay a need for surgical treatment of the patient with BPH is described, the method comprising administering a therapeutically effective amount of an inhibitor of IGF-I activity to the patient with BPH, wherein the inhibitor of IGF-I activity is somatostatin 14, a somatostatin analog, or a small molecule IGF-I receptor kinase specific inhibitor and the therapeutically effective amount of the inhibitor of IGF-I activity is administered to reduce the amount of prostatic hyperplastic tissue in the patient and thereby delay the need for surgical treatment of the patient to reduce the amount of prostatic hyperplastic tissue in the patient. In a particular embodiment thereof, the somatostatin analog is selected from SOM230, BIM23A779, KE108, AN-238, and RC-121. As described herein, the small molecule IGF-I receptor kinase specific inhibitor may be PQ401. In an embodiment thereof, the therapeutically effective amount of the inhibitor of IGF-I activity is administered via a pharmaceutical composition comprising the therapeutically effective amount of the inhibitor of IGF-I activity and a pharmaceutically acceptable carrier. In another embodiment, the pharmaceutical composition consists essentially of the therapeutically effective amount of an inhibitor of IGF-I activity. In a more particular embodiment, the subject is a human.

In yet another aspect, a method for treating benign prostatic hyperplasia (BPH) disease in a patient with BPH is presented, wherein the patient is in need of surgical treatment to reduce the amount of prostatic hyperplastic tissue in the patient, the method comprising administering a therapeutically effective amount of an inhibitor of IGF-I activity to the patient with BPH, wherein the inhibitor of IGF-I activity is somatostatin 14, a somatostatin analog, or a small molecule IGF-I receptor kinase specific inhibitor and the therapeutically effective amount of the inhibitor of IGF-I activity is administered to reduce the amount of prostatic hyperplastic tissue in the patient prior to the surgical treatment, thereby minimizing the surgical treatment required to further reduce the amount of prostatic hyperplastic tissue in the patient. In a particular embodiment thereof, the somatostatin analog is selected from SOM230, BIM23A779, KE108, AN-238, and RC-121. As described herein, the small molecule IGF-I receptor kinase specific inhibitor may be PQ401. In an embodiment thereof, the therapeutically effective amount of the inhibitor of IGF-I activity is administered via a pharmaceutical composition comprising the therapeutically effective amount of the inhibitor of IGF-I activity and a pharmaceutically acceptable carrier. In another embodiment, the pharmaceutical composition consists essentially of the therapeutically effective amount of an inhibitor of IGF-I activity. In a more particular embodiment, the subject is a human.

In another embodiment of the method of the invention, a nucleic acid encoding a peptide inhibitor of IGF-I is administered, and in a related embodiment, an antisense sequence or catalytic RNA capable of interfering with the expression of a gene encoding IGF-I is administered. In further embodiments, inhibition of IGF-I is achieved with a combination of these approaches, for example, administration of an inhibitor of IGF-I activity and an antisense molecule capable of interfering with the expression of IGF-I synthesis. In the treatment method of the invention, an IGF-I inhibitor may be provided systemically or locally, by short or long term administration.

Other objects and advantages will become apparent from a review of the ensuing detailed description taken in conjunction with the following illustrative drawing.

DETAILED DESCRIPTION OF THE INVENTION

Figure 1:
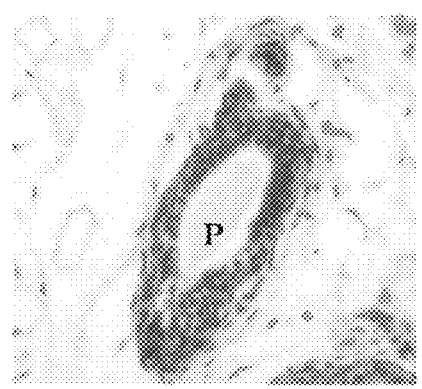
FIG. 1 is a photomicrograph of a histological section of prostate from castrated IGF-I$^{(-/-)}$ knockout mice treated for 7 days with placebo.

Before the present methods and compositions are described, it is to be understood that this invention is not limited to particular methods, compositions, and experimental conditions described, as such methods and compounds may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "an inhibitor of IGF-I activity" may include mixtures of such inhibitors, reference to "the formulation" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

DEFINITIONS

In the context of the present invention, the term "inhibitor" of IGF-I activity is a compound that interferes with the biological activity of IGF-I or effectively reduces the amount of IGF-I circulating in the body or present in a specific tissue. For example, the inhibitor may be a somatostatin (e.g., SS-14) or an analog thereof (e.g., SOM230, BIM23A779, AN-238, and RC-121; excluding octreotide and lanreotide in particular circumstances), an IGFBP (e.g., IGFBP-1), or a combination thereof, a growth hormone antagonist (e.g., pegvisomant), or an antibody to IGF-I such as αIR-3. As indicated herein above, in a particular embodiment, octreotide or lanreotide may be excluded from the list of inhibitors envisioned for use in methods described herein. It is to be understood that the above indicated categories of inhibitors of IGF-I activity are not intended to limit the aforementioned inhibitors with regard to function. A skilled practitioner would, for example, appreciate that a somatostatin analog may, for example, be considered a growth hormone antagonist in that somatostatin analogs are known to inhibit secretion of growth hormone. In another embodiment, the inhibitor of IGF-I activity interferes with post receptor effects of IGF-I action or with the intracellular signaling of IGF-I. In further embodiments, the inhibitor of IGF-I activity is an agent capable of decreasing the rate of IGF-I synthesis, increasing the rate of IGF-I degradation, or increasing the rate of IGF-I clearance from the body. In another embodiment, an inhibitor of IGF-I activity is a nucleic acid molecule which interferes with the expression of a gene encoding IGF-I.

In a particular embodiment, the inhibitor of IGF-I activity is a somatostatin analog (e.g., SOM230), IGFBP1, IGFBP5, or a small molecule IGF-I receptor kinase specific inhibitor (e.g. PQ401).

The term "benign prostatic hyperplasia" ("BPH") is generally used to describe clinical enlargement of the prostate or lower urinary tract, characterized by clinical symptoms comprising irritative or obstructive voiding pattern, urinary retention, and/or frequent urination with an increased residual urine volume.

The term "substantially pure," when referring to a polypeptide, means a polypeptide that is at least 60%, by weight, free from the proteins and naturally-occurring organic molecules with which it is naturally associated. A substantially pure IGF-1 inhibitor is at least 75%, more preferably at least 90%, and most preferably at least 99%, by weight, IGF-1 inhibitor. A substantially pure inhibitor of IGF-1 activity, can be obtained, for example, by chemical synthesis or by isolation from natural sources. Purity can be measured by any appropriate method, e.g., column chromatography, polyacrylamide gel electrophoresis, or HPLC analysis.

"Treatment" refers to the administration of medicine or the performance of medical procedures with respect to a patient, particularly with the infirmity or malady in the instance where the patient is afflicted. In the context of the present invention, treatment includes reduction in the amount of prostatic hyperplasic tissue and amelioration of adverse or undesirable symptoms associated with BPH such as those described herein and known in the art. Treatment may further reduce or delay the need for surgical treatment of BPH to alleviate adverse symptoms in a patient suffering from BPH. Moreover, if treatment with a compound that inhibits IGF-I action reverses symptoms of BPH it might help delay the need for surgery temporarily or indefinitely.

The invention provides methods for treating patients afflicted with BPH comprising administering to a subject a therapeutically effective amount of a compound identified herein. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, mice, rats, etc., and is preferably a mammal, and most preferably male human. In a specific embodiment, a non-human mammal is the subject. In a particular embodiment thereof, the non-human mammal provides an animal model system of BPH, wherein BPH is spontaneous or experimentally induced.

A "therapeutically effective amount" is an amount of a reagent sufficient to achieve the desired treatment effect. In this case the desired effect of the therapeutically effective amount of the reagent would be a reduction in size of the fibromuscular tissue in the prostate in order to relieve the obstructive and irritative symptoms caused by BPH. These would be recognized by a reduction in adverse symptoms and perhaps a reduction in residual urine in the bladder.

General Aspects of the Invention

Recent epidemiological evidence supports the possibility that IGF-I plays a role in either stimulating development or fostering growth of prostate cancer. A positive association between serum concentrations of IGF-1 and prostate cancer risk has been reported (Chan et al. (1998) Science 279:563-566). A question arises whether this possible effect of IGF-I on prostate cancer is specific, like that of testosterone (T) which affects both the growth and development of normal prostate and prostate cancer (Cunha et al. (1987) Endocr. Rev. 8:328-362) or whether it is nonspecific. Although prostate cancer cell growth is stimulated by IGF-I in culture, there has been little direct evidence that IGF-I has a role in the development or integrity of the normal prostate gland or the pathogenesis or furtherance of prostate cancer. It has been postulated that IGF-I, or IGF-II, through the IGF-I receptor, can inhibit apoptosis and therefore maintain an increased number of prostate cancer cells.

Ruan et al. (1999) Endocrinology 140:1984-1989 studied the role of IGF-I in prostate development by examining prostate glandular architecture in IGF-I$^{-/-}$ null mice and wild-type littermates. Glands from 42-day-old IGF-I-deficient animals were not only smaller than those from wild-type mice, but also had fewer terminal duct tips and branch points and deficits in tertiary and quaternary branching, indicating a specific impairment in gland structure. Administration of des(1-3)-IGF-I for 7 days partially reversed the deficit by increasing those parameters of prostate development. IGF-I production was likely to mediate an effect of growth hormone (GH) in this process, as indicated by the observations that GH antagonist transgenic mice also had significantly impaired prostate development and that GH had no independent effect on stimulating prostate development in IGF-I null animals. The data indicated that IGF-I deficiency was the proximate cause of impaired prostate development.

To delineate further the separate and combined effects of T and IGF-I on prostate glandular development, experiments were performed with castrated IGF-I$^{-/-}$ null and wild-type littermates. It was found that both IGF-I and T had significant effects on increasing the number of TDTs, the area of the prostate gland, and the number of branches. These studies, however, evaluated the gross appearance of the glandular tree of the prostate.

Figure 2:
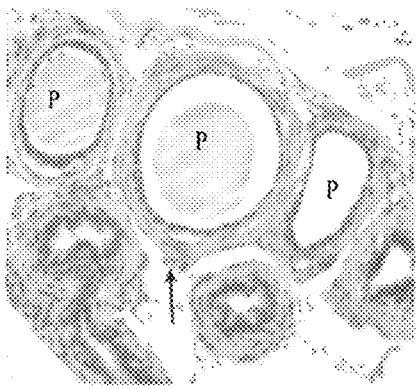
FIG. 2 is a photomicrograph of a histological section of prostate from castrated IGF-I$^{(-/-)}$ knockout mice treated for 7 days with des (1-3) IGF-I.
Figure 3:
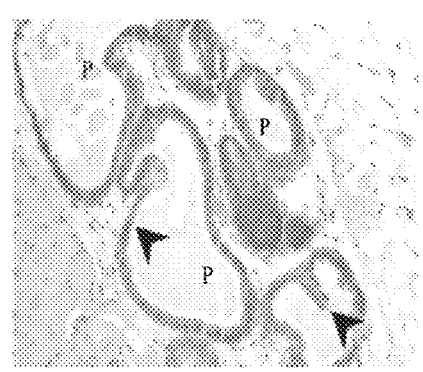
FIG. 3 is a photomicrograph of a histological section of prostate from castrated IGF-I$^{(-/-)}$ knockout mice treated for 7 days with testosterone (T).

As described below, experiments were conducted which resulted in the discovery that the development of fibromuscular tissue of the prostate is under the specific control of IGF-I. While testosterone has long been known to affect prostate development, and IGF-I has only recently been found to play a definite role in prostate development, no direct evidence has ever been presented that IGF-I has a specific effect of development of the fibromuscular layer in the prostate. Further, the experiments described below also show that the effects of T and IGF-I on prostate development are different. In contrast to the effects of IGF-I (FIG. 2), T was not found to have an effect on fibromuscular development, but rather only on intraluminal glandular development (FIG. 3). These new findings are presented in Table 1. Interestingly, these findings appear to explain why 5α-reductase inhibitors have not been more effective in the treatment of BPH. The findings presented herein show that 5α-reductase inhibitors would only be effective in reducing gland size, but not fibromuscular hyperplasia. In contrast, these results suggest that inhibitors of IGF-I could be used to reduce fibromuscular hyperplasia and thereby confer symptomatic relief to a subject with BPH, whether experimentally induced or spontaneous in nature.

To explore the above further, the present inventors performed experiments with inhibitors of IGF-1 activity to assess if such agents can reduce the size of the fibromuscular compartment in vivo. Results presented in Example 4 demonstrate that IGFBP-1, an inhibitor of IGFBP-1 activity, prevents GH induced fibromuscular and glandular development of the prostate in Ames dwarf male animals and inhibits multiple aspects of prostate development in both the fibromuscular and glandular compartments of intact male mice. Accordingly, these findings demonstrate that IGFBP-1 inhibits the normal development of the fibromuscular compartment in eugonadal intact mice and therefore support the likelihood that IGF-I inhibition would be effective in reducing the size of the fibromuscular/stromal compartment of the prostate in the presence of physiological concentrations of IGF-I and circulating testosterone. These results are also viewed as predictive that administration of inhibitors of IGF-I activity to a male subject afflicted with BPH will confer symptomatic relief to the subject by reducing the enlarged fibromuscular/stromal compartment of the prostate that is associated with BPH symptoms.

To explore the above further, the present inventors performed experiments with inhibitors of IGF-I to assess if such agents can reduce the size of the fibromuscular compartment in vivo. The results presented in Example 5 demonstrate that both SS14 and PQ401 reduce the size of various compartments of the prostate to a significant degree in animal model systems. The reduction in size of the fibromuscular compartment is particularly noteworthy in light of its role in BPH. Indeed, each of SS14 and PQ401 reduce the size of both the circular and the longitudinal muscles of the prostate, the enlargement of which muscle layers causes BPH. See, for example, Table 9. The reduction in prostate size is targeted particularly to the prostate as evidenced by the fact that overall body weight is not reduced to a similar extent. See, for example, Table 10. In sum, these results show that both SS14 and PQ401 reduce the size (in terms of weight), area, and individual anatomic components of the prostate in mice and, therefore, could be used advantageously to target the muscles of the prostate whose enlargement in BPH and animal models thereof contribute to symptoms of the condition.

To evaluate further the efficacy of somatostatin 14 (SS-14) in the treatment of BPH and related urinary tract obstruction, the present inventors used an animal model system in which prostate hyperplasia, together with prostatitis is induced by administration of estradiol to male Wistar rats. The estradiol-treated Wistar rat animal model system was originally described by Robinette (1988, The Prostate 12:271-286; the content of which is incorporated herein in its entirety) as offering an animal model of the inflammation and fibromuscular growth observed in human BPH. Robinette also described the estradiol-treated Wistar rat animal model system as useful for identifying factors and/or xenobiotics that can inhibit or potentially reverse progression of prostatic fibromuscular proliferation. Wilson et al. (Exp Mol Pathol. 2004; 77:7-17; the content of which is incorporated herein in its entirety) affirmed that the estradiol-treated Wistar rat animal model system of Robinette (supra) was an accepted animal model for human BPH. Indeed, Wilson et al. state that chronic inflammation induced in the lateral prostate by estrogen treatment is accompanied later by fibromuscular proliferation, which correlates with the prevalence of chronic inflammation in BPH in men.

The present inventors modified the protocol of Robinette to substitute "medical castration", an art recognized equivalent castration method, in place of surgical castration. In so doing, the present inventors opted for a less invasive approach to achieve castration of the rats. The substitution was based on the well accepted principle that administration of estradiol inhibits production of luteinizing hormone (LH) from the pituitary and LH controls testosterone secretion from the testes. In the absence of LH, testosterone falls to castrate levels. See, for example, Piacsek and Meites (Endocrinology 79:432-439, 1966) and Couse and Korach (Endocrine Reviews 20:358-417, 1999), the entire content of each of which is incorporated herein. Further to this point, the present inventors were also aware of disclosures, such as, for example, Naslund et al. (1988, J Urol 140:1049-1053; the entire content of which is incorporated herein), which disclosed that administration of exogenous estradiol-17β (medical castration) increased the incidence and severity of prostatitis in old Wistar rats from 27% to 100% (p less than 0.01) and surgical castration had a similar effect. The present inventors were also motivated to avoid surgical castration in light of restrictions on invasive procedures as enforced by decisions governing acceptable practice in laboratory research involving animals. Given all of the above, the present inventors understood medical castration to be the equivalent of surgical castration with regard to inducing hyperplasia of the prostate in male Wistar rats.

The present inventors also took other equally effective steps to reduce unnecessary experimentation in the estradiol-treated male Wistar rats. Since estradiol treatment is known to be at least as effective as testosterone in reducing serum LH to levels that result after castration in the male (Couse and Korach, Endocrine Reviews 20:358-417, 1999 and Gharib et al., Endocrine Reviews, 1990, 177-199), and the prostates of the estradiol-treated male Wistar rats clearly exhibited features characteristic of benign prostatic hyperplasia, the present inventors elected to employ shorter term treatment with estradiol alone, without adding testosterone. The Robinette reference suggests this alternative methodology in that it states that chronic administration of estradiol, either alone or in combination with DHT, induces stromal proliferation that comprises smooth muscle cells, fibroblasts and large quantities of collagen. Accordingly, the present inventors opted for the approach involving administration of estradiol alone as described by Robinette.

In order to recapitulate BPH temporally as it occurs in human males, the present inventors utilized 3 months old male Wistar rats, at which time adult prostate formation has already taken place. Given that BPH occurs only in adult men, the decision to use 3 month old rats, rather than 1 week old rats as described in Robinette, was determined to be a logical experimental approach. Indeed, Robinette recognizes that the experimental responses observed in rats treated as described therein reflect the changes seen in the aging rat as well as parallel features of human BPH and thus, statements directed to these points were interpreted as suggesting the potential for using aging rats. Various references, such as, for example, Lundgren et al. (1984, The Prostate 5: 277-284) also influenced this decision. Indeed, Lundgren et al. described the use of older male Wistar rats for studies relating to inflammation of the prostate since these rats develop nonacute, age-dependent prostatitis with high frequency. It is also noteworthy that since 3 month old animals are exposed to endogenous testosterone, which drives prostate development, this choice further obviates the requirement for administration of exogenous testosterone.

As described in greater detail herein below and depicted in the drawings, results presented herein confirm and corroborate that the histological and morphological changes to the prostate, which are characteristic of human BPH, are essentially identical in the surgically castrated, estradiol-treated Wistar rats of Robinette and the estradiol-treated (medically castrated) Wistar rats described herein.

Figure 8:
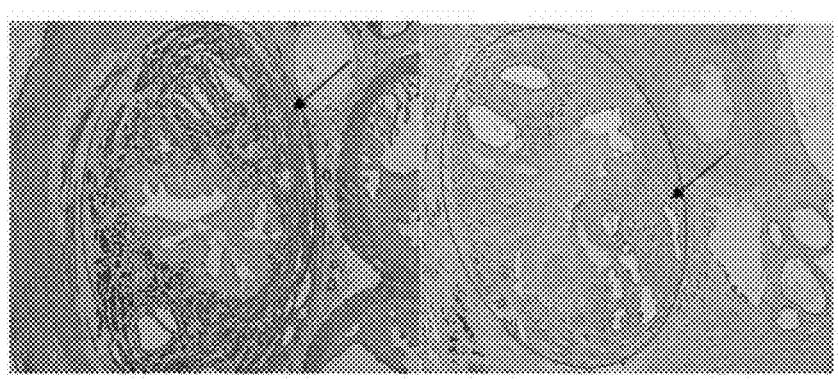
FIG. 8 presents photomicrographs depicting the effect of SS-14 on the fibromuscular compartment surrounding the urethra in an animal representative of an animal model system for human BPH. Transverse sections of the urethra from a representative rat treated with $E_2$ (left panel) and a rat treated with $E_2$+SS-14 (right panel) are shown. The urethras are encircled in blue line. Within the urethra there is an outer encasement of fibromuscular tissue. The smooth muscle is immunostained in brown (arrows). Note that the amount of smooth muscle is lower in the animal also treated with SS-14. This represents a diminution in the fibromuscular compartment. Arrowheads point to the central glandular tissue surrounding the urethral lumen

As depicted in FIG. 8, treatment of the older eugonadal male Wistar rats with estradiol ($E_2$) stimulated development of prostate hyperplasia as evident in the significant degree of inflammation and fibromuscular growth observed in the prostates of these animals. The extent of prostate hyperplasia was also apparent in the total weight of the prostate.

As determined in a first set of experiments, SS14 (an inhibitor of IGF-I activity) treatment of the $E_2$-treated male Wistar rats resulted in a significant reduction in prostate weight ($p=0.024$) as compared to control $E_2$-treated rats (rats treated with vehicle only). These results demonstrate that SS14 reduces prostate weight and gland size to a significant degree in a model of estrogen induced rat prostatitis and benign prostatic hyperplasia caused by treatment with $E_2$.

Additional studies revealed that treatment with SS-14 significantly reduces whole prostate weight in $E_2$.treated male Wistar rats relative to control $E_2$.treated male Wistar rats, thereby confirming the initial studies and reaffirming that SS14 treatment reduces the prostate organ overall. See, for example, Table 11, which shows that treatment with SS-14 significantly reduces prostate weight when added to $E_2$.treated rats ($p=0.019$), demonstrating that it reduces the whole organ bulk.

The effect of SS-14 treatment on the total area of prostate occupied by prostate glandular tissue (also referred to herein as glands) was also assessed. To determine whether SS-14 has an inhibitory effect on the glandular component of the prostate, the area of the organ occupied by glands was measured in transverse sections. Such transverse sections included the urethra and were cut at the level at which the width of the prostate was maximal. Gland area is expressed as it relates to the total area of the organ in transverse sections. See, for example, Table 12, which shows that SS-14 significantly reduces the area occupied by glands ($p=0.028$). These results reveal that SS-14 has an independent effect on reducing gland size in this animal model of human BPH.

The effect of SS-14 on the fibromuscular compartment surrounding the urethra was also evaluated. To determine whether SS-14 reduced the fibromuscular component of the urethra, tissue sections were immunostained for smooth muscle α actin (αSMA). Each prostate was cut at 5 different levels, with 150 microns between each set of sections. The results of aSMA staining are shown in the photomicrographs depicted in FIG. 8. The whole urethra is indicated by circles and the surrounding fibromuscular layer by arrows. FIG. 8 shows representative sections from one animal treated with $E_2$ (left) vs one treated with $E_2$+SS-14. As shown therein, the amount of smooth muscle surrounding the prostate is greatly diminished in the SS-14 treated animal. This reveals that SS-14 treatment significantly reduces the volume of the fibromuscular compartment of the enlarged prostate in this animal model of human BPH. These results are also presented in numerical fashion in Table 13. The discovery that SS-14 can reduce the volume of the fibromuscular compartment in this animal model of BPH is significant from a therapeutic point of view because hyperplasia of the fibromuscular compartment has been identified as a characteristic feature of human BPH that contributes directly to adverse symptoms associated therewith.

Further to the above, the fibromuscular tissue surrounding the urethra is a compartment of the prostate known to be involved in the etiology of human BPH. By way of background, the fibromuscular tissue surrounding the urethra and urethral lumen is enlarged (hyperplastic) in human BPH, a feature which is recapitulated in the animal model described herein, and this enlargement leads to narrowing of the urethral lumen. Narrowing of the urethral lumen contributes to many symptoms of human BPH, such as, irritative or obstructed voiding pattern, urinary retention, and frequent urination with an increased residual urine volume. Accordingly, a reduction in the fibromuscular tissue surrounding the urethra due to administration of an inhibitor of IGF-I activity, such as SS14, results in less constriction of the urethra and a resultant opening of the lumen of the urethra that facilitates improved urine flow. As a result, the inhibitor of IGF-I activity confers therapeutic relief to a subject with BPH.

In light of the above, the present inventors have shown that inhibition of IGF-I activity using three different exemplary IGF-1 inhibitors (agents/compounds), namely, IGFBP-1, SS14 and PQ401, inhibits prostate development and growth in a number of animal models, including: Ames Dwarf animals treated with GH to develop the prostate; normal male mice at 28 days of age (treated with IGFBP-1); male mice treated with SSI4 or PQ401; and in older male Wistar rats treated with estradiol (an animal model of BPH), which were treated with or without SS14. Although not wishing to be bound by theory, results presented herein suggest that IGF-I inhibitors inhibit or reduce prostate size by inhibiting cell proliferation and increasing apoptosis. The net result being that IGF-I inhibitors can reduce the compression/restriction of the urethra due to enlargement of the fibromuscular tissue and thereby promote improved urine flow and complete voiding thereof.

In light of the above, a sound prediction can be made that administering a therapeutically effective amount of an inhibitor of IGF-I activity to a patient with BPH will effect a reduction in the amount of prostatic hyperplastic tissue and alleviation of adverse symptoms of BPH in the patient following treatment. Moreover, based on the results in rats and mice, it is reasonable to predict that IGF-I inhibition will reduce prostate size in human males and/or prevent growth of the prostate. Such treatment would also confer symptomatic relief for urinary obstruction characteristic of BPH and would, moreover, be useful in reducing prostate size to delay the need for surgical intervention and/or make enlarged prostates more amenable to less invasive surgical intervention.

Methods for Making Somatostatin Analogs or Obtaining Same

The somatostatin analog SOM230 can be obtained from Novartis. Alternatively, the cyclohexapeptide can be synthesized using protocols known to skilled practitioners.

Somatostatin 14 can be obtained from Anaspec or can be isolated or synthesized using protocols known to skilled practitioners.

AN-238 and RC-121 and methods of making same were described in, for example, Nagy et al. (Proc Natl Acad Sci, 1998, Vol 95, pp 1794-1799), the entire content of which is incorporated herein in its entirety.

Ke108, for example, can be made using the following synthetic protocol:

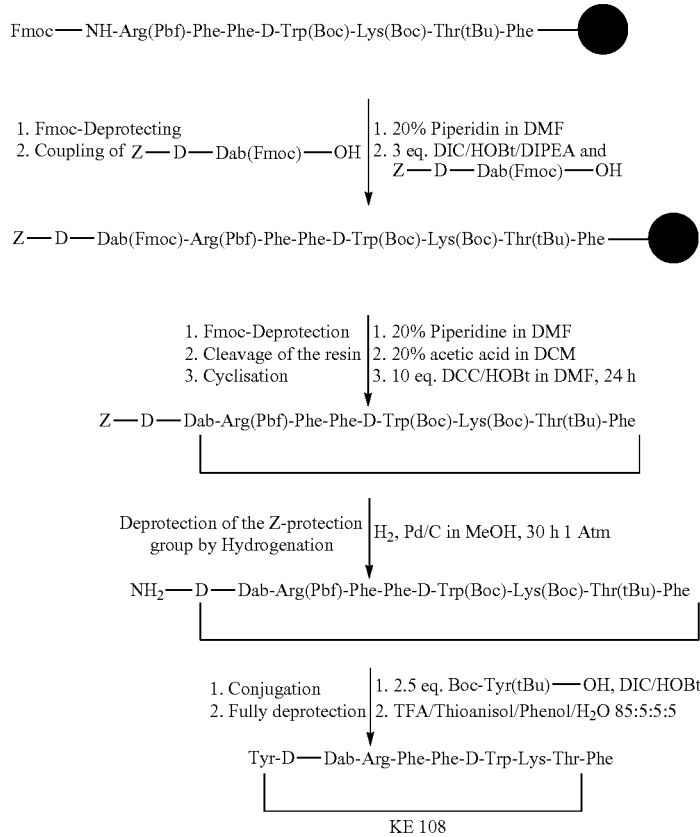

See also Reubi et al. (Eur. J. Pharm., 2002, 456:45-49), the entire content of which is incorporated herein in its entirety.

PQ401 and other diaryl urea compounds are available and can be obtained from a variety of suppliers, including: Telik Corp. (Palo Alto, Calif.); Tocris bioscience; Sigma-Aldrich; and Enzo Life Sciences. See, for example, Gable et al., 2006, Mol Cancer Ther 5:1079-1086; Anderson et al., 2006, J Comb Chem 8:784; and Sivakumar et al., 2009, Int J Oncol 34:329, the entire content of each of which is incorporated herein by reference.

Methods of Treating BPH and Methods of Administration

The invention provides methods of treatment comprising administering to a subject an effective amount of an inhibitor of IGF-I activity. In a preferred aspect, the inhibitor compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In one specific embodiment, a non-human mammal is the subject and may be utilized as an animal model system of BPH. Such model systems may present with BPH symptoms spontaneously or BPH symptoms may be experimentally induced therein. In another specific embodiment, a human mammal is the subject. The invention further provides methods of treatment comprising administering to a subject an effective amount of an inhibitor of IGF-I activity in combination with a testosterone inhibitor, a 5α-reductase inhibitor, and/or an agent or compound that has an anti-proliferative or anti-mitogenic effect.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous (iv), subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In a particular embodiment wherein the compound has a short half-life (such as, e.g., SS14, IGFBP1, or IGFBP5), the compound may be administered intravenously (e.g., via a continuous iv drip) or by direct injection into the prostate. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, or fibers or co-polymers such as Elvax (see Ruan et al, 1992, Proc Natl Acad Sci USA, 89:10872-10876). In one embodiment, administration can be by direct injection by aerosol inhaler.

In another embodiment, the inhibitor compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the inhibitor compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

The present invention also provides pharmaceutical compositions for the treatment of BPH. Such compositions comprise a therapeutically effective amount of an agent able to interfere with the biological activity of IGF-I, and a pharmaceutically acceptable carrier. Compositions of the present invention may comprise one or more IGF-I inhibitors. In a further embodiment the pharmaceutical compositions of the present invention further comprise, in addition to one or more IGF-I inhibitors, a testosterone inhibitor, a 5α-reductase inhibitor, and/or an agent or compound that has an anti-proliferative or anti-mitogenic effect. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The therapeutic compounds useful in the method of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound useful in the method of the invention which will be effective in the treatment of BPH and related disorders can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

Therapeutic Uses of IGF-1 Inhibitors

The invention provides for treatment, prevention or amelioration of BPH disorder by administration of a therapeutic agent capable of inhibiting IGF-I activity.

A change in IGF-I-induced fibromuscular hyperplasia due to the administration of such compounds can be readily detected, e.g., by measurement of the prostrate gland, or diminishing of undesirable symptoms. Such assays or evaluations can be performed before and after the administration of the compound as described herein. Ultrasound can be used to measure prostate glands, but clinical improvement in symptoms experienced by patients is the most important result. These include reduction in irritative and obstructive symptoms and signs. This includes a reduction in residual urine in the urinary bladder, measurable by radiological techniques.

In one embodiment, a nucleic acid comprising a sequence encoding a peptide or protein inhibitor of IGF-I activity is administered. In another embodiment, a nucleic acid sequence encoding an inhibitor capable of blocking the activity of IGF-I is administered. In yet another embodiment, a nucleic acid sequence encoding a stimulator of IGF binding protein, for example IGFBPI, is administered. Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; and Morgan and Anderson (1993) Ann. Rev. Biochem. 62:191-217; May (1993) TIBTECH 11(5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In a particular aspects, the compound comprises a nucleic acid encoding a peptide or protein inhibitor of IGF-I synthesis, such nucleic acid being part of an expression vector that expresses the peptide or protein in a suitable host. In particular, such a nucleic acid has a promoter operably linked to the coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller and Smithies (1989) Proc. Natl. Acad. Sci. USA 86:8932-8935; Zijlstra et al. (1989) Nature 342:435-438).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu and Wu, 1987, J. Biol. Chem. 262:4429-4432), which can be used to target cell types specifically expressing the receptors.

In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al. (1989) Nature 342: 435-438).

In a further embodiment, a viral vector that contains a nucleic acid encoding an inhibitor of IGF-I activity, for example, a retroviral vector can be used (see Miller et al. (1993) Meth. Enzymol. 217:581-599). These retroviral vectors have been modified to delete retroviral sequences that are not necessary for packaging of the viral genome and integration into host cell DNA. The nucleic acid encoding the enzyme to be used in gene therapy is cloned into the vector, which facilitates delivery of the gene into a subject. More detail about retroviral vectors can be found in Boesen et al. (1994) Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al. (1994) J. Clin. Invest. 93:644-651; Kiem et al. (1994) Blood 83:1467-1473; Salmons and Gunzberg (1993) Human Gene Therapy 4:129-141; and Grossman and Wilson (1993) Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993) Current Opinion in Genetics and Development 3:499-503 present a review of adenovirus-based gene therapy. Bout et al. (1994) Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al. (1991) Science 252:431-434; Rosenfeld et al. (1992) Cell 68:143-155; Mastrangeli et al. (1993) J. Clin. Invest. 91:225-234; PCT Publication WO94/12649; and Wang, et al. (1995) Gene Therapy 2:775-783. Adeno-associated virus (AAV) has also been proposed for use in gene therapy (Walsh et al. (1993) Proc. Soc. Exp. Biol. Med. 204:289-300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr (1993) Meth. Enzymol. 217:599-618; Cohen et al. (1993) Meth. Enzymol. 217:618-644; Cline (1985) Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. In a preferred embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The amount of cells envisioned for use depends on the desired effect, the condition of the subject, etc., and can be determined by one skilled in the art.

Cells into which a nucleic acid can be introduced for purposes of gene therapy encompass any desired, available cell type, and include but are not limited to neuronal cells, glial cells (e.g., oligodendrocytes or astrocytes), epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood or fetal liver. In a preferred embodiment, the cell used for gene therapy is autologous to the subject that is treated.

In an embodiment in which recombinant cells are used in gene therapy, a nucleic acid encoding an inhibitor of IGF-I activity, or an inhibitor of IGF-I synthesis, or an agent capable of increasing the rate of IGF-I degradation, is introduced into the cells such that it is expressible by the cells or their progeny, and the recombinant cells are then administered in vivo for therapeutic effect. In a specific embodiment, stem or progenitor cells are used. Any stem or progenitor cells which can be isolated and maintained in vitro can be used in accordance with this embodiment of the present invention (see e.g. PCT Publication WO 94/08598, dated Apr. 28, 1994; Stemple and Anderson (1992) Cell 71:973-985; Rheinwald (1980) Meth. Cell Bio. 21A:229; and Pittelkow and Scott (1986) Mayo Clinic Proc. 61:771).

In another embodiment, the nucleic acid to be introduced for purposes of gene therapy may comprise an inducible promoter operably linked to the coding region, such that expression of the nucleic acid is controllable by controlling the presence or absence of the appropriate inducer of transcription.

Direct injection of a DNA coding for an inhibitor of IGF-I activity, an inhibitor of IGF-I synthesis, or an agent capable of increasing the rate of IGF-I degradation may also be performed according to, for example, the techniques described in U.S. Pat. No. 5,589,466. These techniques involve the injection of "naked DNA", i.e., isolated DNA molecules in the absence of liposomes, cells, or any other material besides a suitable carrier. The injection of DNA encoding a protein and operably linked to a suitable promoter results in the production of the protein in cells near the site of injection and the elicitation of an immune response in the subject to the protein encoded by the injected DNA.

In one embodiment of the invention, BPH is treated or prevented by administration of a compound that inhibits the activity of IGF-I. Compounds useful for this purpose may include antibodies directed to IGF-I (and fragments and derivatives containing the binding region thereof), and antisense or ribozyme nucleic acids.

The present invention provides the therapeutic or prophylactic use of nucleic acids comprising at least six nucleotides that are antisense to a gene or cDNA encoding IGF-I, or a portion thereof. As used herein, an "antisense" nucleic acid refers to a nucleic acid capable of hybridizing by virtue of some sequence complementarity to a portion of an RNA (preferably mRNA) encoding IGF-I. The antisense nucleic acid may be complementary to a coding and/or noncoding region of an mRNA encoding IGF-I. Such antisense nucleic acids have utility as compounds that inhibit expression of a gene encoding IGF-I, and can be used in the treatment or prevention of IGF-I induced fibromuscular hyperplasia.

The antisense nucleic acids of the invention are double-stranded or single-stranded oligonucleotides, RNA or DNA or a modification or derivative thereof, and can be directly administered to a cell or produced intracellularly by transcription of exogenous, introduced sequences.

The antisense nucleic acids are of at least six nucleotides and are preferably oligonucleotides ranging from 6 to about 50 oligonucleotides. In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof and can be single-stranded or double-stranded. The oligonucleotide can be modified at the base moiety, sugar moiety, or phosphate backbone. The oligonucleotide may include other appended groups such as peptides; agents that facilitate transport across the cell membrane (see, e.g., Letsinger et al. (1989) Proc. Natl. Acad. Sci. USA 86:6553-6556; Lemaitre et al. (1987) Proc. Natl. Acad. Sci. 84:648-652; PCT Publication No. WO 88/09810, published Dec. 15, 1988) or blood-brain barrier (see, e.g., PCT Publication No. WO 89/10134, published Apr. 25, 1988); hybridization-triggered cleavage agents (see, e.g., Krol et al. (1988) BioTechniques 6:958-976) or intercalating agents (see, e.g., Zon (1988) Pharm. Res. 5:539-549). In a particular aspect of the invention, an antisense oligonucleotide is provided, preferably of single-stranded DNA. The oligonucleotide may be modified at any position on its structure with substituents generally known in the art.

The antisense oligonucleotide may comprise any suitable of the following modified base moieties, e.g., 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, and other base analogs.

In another embodiment, the oligonucleotide comprises at least one modified sugar moiety, e.g., one of the following sugar moieties: arabinose, 2-fluoroarabinose, xylulose, and hexose.

In yet another embodiment, the oligonucleotide comprises at least one of the following modified phosphate backbones: a phosphorothioate, a phosphorodithioate, a phosphoramidothioate, a phosphoramidate, a phosphordiamidate, a methylphosphonate, an alkyl phosphotriester, a formacetal, or an analog of formacetal.

In yet another embodiment, the oligonucleotide is an, α-anomeric oligonucleotide. An, α-anomeric oligonucleotide forms specific double-stranded hybrids with complementary RNA in which, contrary to the usual, β-units, the strands run parallel to each other (Gautier et al. (1987) Nucl. Acids Res. 15:6625-6641).

The oligonucleotide may be conjugated to another molecule, e.g., a peptide, hybridization triggered cross-linking agent, transport agent, or hybridization-triggered cleavage agent.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, and methylphosphonate oligonucleotides can be prepared by use of controlled pore glass polymer supports (Sarin et al. (1988) Proc. Natl. Acad. Sci. USA 85:7448-7451).

In another embodiment, the antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Examples of such promoters are outlined above.

The antisense nucleic acids of the invention comprise a sequence complementary to at least a portion of an RNA transcript of a gene encoding IGF-I, preferably a human gene encoding IGF-I, however, absolute complementarity, although preferred, is not required. A sequence "complementary to at least a portion of an RNA," as referred to herein, means a sequence having sufficient complementarity to be able to hybridize under stringent conditions (e.g., highly stringent conditions comprising hybridization in 7% sodium dodecyl sulfate (SDS), 1 mM EDTA at 65° C. and washing in 0.1×SSC/0.1% SDS at 68° C., or moderately stringent conditions comprising washing in 0.2×SSC/0.1% SDS at 42° C. with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA encoding an enzyme involved in glucosylceramide synthesis it may contain and still form a stable duplex (or triplex, as the case may be). One skilled in the art can ascertain a tolerable degree of mismatch by use of standard procedures to determine the melting point of the hybridized complex.

Pharmaceutical compositions of the invention, comprising an effective amount of an antisense nucleic acid of the invention in a pharmaceutically acceptable carrier, vehicle or diluent can be administered to a subject in need thereof. The amount of antisense nucleic acid which will be effective in the treatment of IGF-I induced fibromuscular hyperplasia can be determined by standard clinical techniques.

Inhibitory Ribozyme and Triple Helix Approaches

In another embodiment, symptoms of BPH may be ameliorated by decreasing the level of IGF-I by using gene sequences encoding IGF-I in conjunction with well-known gene "knock-out," ribozyme or triple helix methods to decrease gene expression of IGF-I. In this approach ribozyme or triple helix molecules are used to modulate the activity, expression or synthesis of the gene encoding IGF-I, and thus to ameliorate the symptoms of the disorder. Such molecules may be designed to reduce or inhibit expression of a mutant or non-mutant target gene. Techniques for the production and use of such molecules are well known to those of skill in the art.

Ribozyme molecules designed to catalytically cleave gene mRNA transcripts encoding IGF-I can be used to prevent translation of target gene mRNA and, therefore, expression of the gene product. (See, e.g., PCT International Publication WO90/11364, published Oct. 4, 1990; Sarver et al. (1990) Science 247:1222-1225).

Ribozymes are enzymatic RNA molecules capable of catalyzing the specific cleavage of RNA. (For a review, see Rossi (1994) Current Biology 4, 469-471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy mRNAs encoding IGF-I, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art and is described more fully in Myers (1995) Molecular Biology and Biotechnology: A Comprehensive Desk Reference, VCH Publishers, New York, (see especially FIG. 4, page 833) and in Haseloff and Gerlach (1988) Nature, 334, 585-591, each of which is incorporated herein by reference in its entirety.

Preferably the ribozyme is engineered so that the cleavage recognition site is located near the 5' end of the mRNA encoding IGF-I, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al. (1984) Science, 224, 574-578; Zaug and Cech (1986) Science, 231, 470-475; Zaug, et al. (1986) Nature, 324, 429-433; published International patent application No. WO 88/04300 by University Patents Inc.; Been and Cech (1986) Cell, 47, 207-216). The Cech-type ribozymes have an eight base pair active site which hybridizes to a target RNA sequence and subsequence cleavage of the target RNA takes place. The invention encompasses those Cech-type ribozymes which target eight base-pair active site sequences that are present in the gene encoding the enzyme involved in glucosylceramide synthesis.

As in the antisense approach, the ribozymes can be composed of modified oligonucleotides (e.g., for improved stability, targeting, etc.) and should be delivered to cells that express the enzyme involved in glucosylceramide synthesis in vivo. A preferred method of delivery involves using a DNA construct "encoding" the ribozyme under the control of a strong constitutive pol III or pol II promoter, so that transfected cells will produce sufficient quantities of the ribozyme to destroy endogenous mRNA encoding the enzyme involved in glucosylceramide synthesis and inhibit translation. Because ribozymes, unlike antisense molecules, are catalytic, a lower intracellular concentration is required for efficacy.

Endogenous expression of IGF-I can also be reduced by inactivating or "knocking out" the gene encoding IGF-I, or the promoter of such a gene, using targeted homologous recombination (e.g., see Smithies et al. 1985) Nature 317: 230-234; Thomas and Capecchi (1987) Cell 51:503-512; Thompson et al. (1989) Cell 5:313-321; and Zijlstra et al. (1989) Nature 342:435-438, each of which is incorporated by reference herein in its entirety). For example, a mutant gene encoding a non-functional IGF-I (or a completely unrelated DNA sequence) flanked by DNA homologous to the endogenous gene (either the coding regions or regulatory regions of the gene encoding IGF-I) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene. However, this approach can be adapted for use in humans provided the recombinant DNA constructs are directly administered or targeted to the required site in vivo using appropriate viral vectors.

Alternatively, the endogenous expression of a gene encoding IGF-I can be reduced by targeting deoxyribonucleotide sequences complementary to the regulatory region of the gene (i.e., the gene promoter and/or enhancers) to form triple helical structures that prevent transcription of the gene encoding an enzyme involved in glucosylceramide synthesis in target cells in the body. (See generally, Helene (1991) Anticancer Drug Des. 6(6), 569-584; Helene et al. (1992) Ann. N.Y. Acad. Sci., 660, 27-36; and Maher (1992) Bioassays 14(12), 807-815).

Nucleic acid molecules to be used in triplex helix formation for the inhibition of transcription in the present invention should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In one embodiment, wherein the antisense, ribozyme, or triple helix molecules described herein are utilized to inhibit mutant gene expression, it is possible that the technique may so efficiently reduce or inhibit the transcription (triple helix) or translation (antisense, ribozyme) of mRNA produced by normal gene alleles of IGF-I that the situation may arise wherein the concentration of IGF-I may be lower than is necessary for a normal phenotype. In such cases, to ensure that substantially normal levels of activity of a gene encoding IGF-I are maintained, gene therapy may be used to introduce into cells nucleic acid molecules that encode and express IGF-I that exhibit normal gene activity and that do not contain sequences susceptible to whatever antisense, ribozyme, or triple helix treatments are being utilized. Alternatively, in instances whereby the gene encodes an extracellular protein, a normal protein can be co-administered in order to maintain the requisite level of activity.

Antisense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Analysis of the Differential Effects of Testosterone and IGF-I on Restoration of Impaired Prostate Development in Dwarf Mice Groups of castrated IGF-I$^{(-/-)}$ null male mice were treated with either vehicle, testosterone in silastic capsules, des(1-3) IGF-I by an infusion through an Alzet pump containing 20 µg per pump, or the combination of testosterone and IGF-I for a period of 7 days.

In order to determine which specific structure was affected by which hormone, entire urogenital complexes were embedded in paraffin blocks, including the prostate glands, coagulating glands, seminal vesicles, urethra, urinary bladder attached to parts of the ureter, vas deferens, and ampullary glands. These were carefully sectioned such that the areas of prostate development could be analyzed.

The prostates were then removed, fixed and examined histologically. Morphometric analysis was carried on 30 cross sections of the prostate taken from five different serial sections. Changes in the area of the lumen, epithelial layer and fibromuscular layer were determined. These counts were performed using a Provis ×70 microscope (Olympus) attached to an Olympus DP10 digital camera. Images were taken using a 20× apochromate objective and were captured digitally at a resolution of 386 pixels. Data were tested for statistical significance using the SPSS statistical computer program (SPSS, Inc., Chicago, Ill.). Since assumptions for a parametric test were not valid (Kolmogorov-Sminov p<0.05), all data were evaluated by Kruskall-Wallis analysis of variance and the Mann-Whitney U test as a multiple comparison method.

Figure 4:
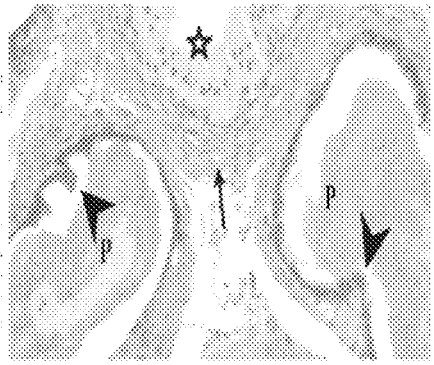
FIG. 4 is a photomicrograph of a histological section of prostate from castrated IGF-I$^{(-/-)}$ knockout mice treated for 7 days with a combination of T and IGF-I.

When T was given alone, the major effect was a marked increase in epithelial elements, which were concluded to be hyperplastic. In contrast, treatment with des(1-3)IGF-I resulted in relatively empty terminal duct tips (TDTs) lined with basal cells. The most marked changes in the tissue from des(1-3)IGF-I treated animals were on the fibromuscular layer of prostate surrounding the TDTs, which gave the appearance of benign prostatic hyperplasia (BPH). The combination of T+IGF-I resulted in what appeared to be normal prostate with TDTs lined with basal cells and epithelial glandular cells around a lumen, with fibromuscular tissue around these glandular elements. The results are shown in the photomicrographs of FIGS. 1-4. FIG. 1 is a control showing the small number of TDTs. FIG. 2 shows the effect of IGF-I alone (* shows a vas deferens). FIG. 3 shows the effects of T alone. FIG. 4 shows the effect of T+IGF-I, encompassing both epithelial glandular elements and surrounding stromal elements.

In further detail, FIG. 1 shows a section of an immature glandular duct from an untreated IGF-I$^{(-/-)}$ castrated male mouse. These ducts are few in number in these animals, they develop in response to hormonal stimulation. FIG. 2 shows the effect of Des(1-3) IGF-I treatment for 7 days increase the number of glands and the area they occupy. The main effect of IGF-I was on fibromuscular hyperplasia (the arrow points to the area of fibromuscular hyperplasia) which surrounds a prostatic glandular ductal structure which has basal cell around the perimeter of the gland. Note that there is little or no intraglandular epithelial hyperplasia. FIG. 3 shows the effect of testosterone alone was on stimulating duct structures containing epithelial glandular hyperplasia. Arrow heads point to these glandular structures. FIG. 4 shows the combination of Des(1-3)IGF-1 and testosterone increased the number of glands and the area they occupy. The combined effect of these two hormones was to increase the lumen size and maintain the fibromuscular hyperplasia layers around the glands.

The results below (shown in TABLE 1) indicate that the main effect of IGF-I is on formation of empty glandular tubes except for basal cells and the fibromuscular layer surrounding the tube. The fibromuscular layer was hyperplastic in response to IGF-I. In contrast, the main effect of testosterone was on intratubular gland development and tube width, presumably through an effect on inducing formation of testosterone sensitive glandular structures from the basal cells. The combination of testosterone and IGF-I caused full development of the prostate that includes glandular structures and connective tissue structures such as fibromuscular tissue.

TABLE 1

Morphometry of sections of prostate glands from IGF-I knockout male animals treated with various hormones or combinations of hormones for 7 days

| Area of each prostatic component (Mean values)Unit µm$^2$ | Percentage |
|---|---|
| CONTROL | |
| Lumen = 57,537.57 | 33 |
| Eptithelium = 71,844.76 | 42 |
| Stroma (connective-muscle) = 43,752.31 | 25 |
| Total = 173,134.64 | |
| DES (1-3) IGF-I | |
| Lumen = 228,325.88 | 42 |
| Eptithelium = 78,158.79 | 15 |
| Stroma (connective-muscle) = 236,626.38 | 43 |
| Total = 543,111.05 | |
| TESTOSTERONE | |
| Lumen = 369,495.45 | 69 |
| Eptithelium = 84,551.64 | 15 |
| Stroma (connective-muscle) = 89,797.254 | 16 |
| Total = 543,844.34 | |
| IGF-I + TESTOSTERONE | |
| Lumen = 491,415 | 70 |
| Eptithelium = 92,420.76 | 13 |
| Stroma (connective-muscle) = 116,575.87 | 16 |
| Total = 700,412 | |

Example 2

The differential effects of hormones IGF-I and testosterone on development of different compartments in the prostate is further demonstrated in assessing IGF-I receptor immunopositive cells in prostate elements. IGF-I and testosterone synergize in stimulating IGF-I receptor staining in epithelial elements but not in fibromuscular elements as shown in TABLE 2.

TABLE 2

| | % IGF-I RECEPTOR IMMUNOPOSITIVE CELLS | |
|---|---|---|
| | EPITHELIUM | FIBROMUSCULAR |
| CONTROL | 0 | 0 |
| IGF-I | 20 ± 0.5 | 100 ± 0.02 |
| TESTOSTERONE | 0 | 95 ± 0.4 |
| IGF-I + TESTOSTERONE | 98 ± 0.06 | 85 ± 0.8 | by Alzet pump) or vehicle. The prostates were then removed and examined as described above. Treatment with bGH increased the number of TDTs from a mean of 48 (controls) to 61 (treated) p=0.011, the area of the gland from 0.71 cm$^2$ to 1.12 (NS), quaternary branching from 35 to 44 (p<0.01) and branch points from 37 to 46 (p=0.011). Similar changes were noted in the dorsal prostate.

IGF-I, as measured by RIA, was detected in homogenates of prostate glands from 87 day old male mice (223 ng/5 prostates). When bGH (200 µg daily for 4 days) was administered IGF-I rose to 418-526 ng/5 prostates. Serum IGF-I was 494 ng/ml in normal male mice. The IGF-I in prostate was likely produced there because bGH increases IGF-I mRNA in prostate.

TABLE 3

| Comparison of prostate development of GH deficient mice and wild-type littermates | | | | |
|---|---|---|---|---|
| | Terminal Duct Tips (TDT) | Area (cm$^2$) | 4°- Branching | Branch Points |
| WT (n = 3) | 57.0 ± 4.3 | 2.2 ± 0.10 | 43.0 ± 3.4 | 47.0 ± 3.7 |
| Ames (n = 3) | 40.0 ± 3.5 [a] | 0.45 ± 0.03 [b] | 30.0 ± 2.7 [a] | 35.0 ± 2.5 [a] |
| WT (n = 5) | 61.0 ± 1.5 | 1.39 ± 0.12 | 40.0 ± 1.2 | 47.0 ± 0.7 |
| bGH tg [c] (n = 5) | 35.4 ± 1.7 [b] | 0.38 ± 0.04 [b] | 16.6 ± 1.9 [b] | 24.8 ± 1.2 [b] |
| WT (n = 5) | 67.0 ± 1.3 | 1.76 ± 0.08 | 47.0 ± 0.5 | 49.0 ± 1.2 |
| Lit/Lit (n = 3) | 48.6 ± 1.1 [b] | 0.71 ± 0.02 [b] | 35.4 ± 1.2 [b] | 37.0 ± 1.2 [b] |

[a] P < 0.05 compare with wild type.
[b] P < 0.0001 compared with wild type
[c] = bGH mutant transgenic mouse.
WT = wild-type Example 3

IGF-I is Essential for Normal Prostate Development

GH-deficient animals demonstrate impaired prostate development. These include transgenic mice overexpressing a GH antagonist (that binds to and inactivates GH receptors making the animals functionally deficient in GH), growth hormone releasing factor receptor (GHRH-R$^{-/-}$) knockout mice (Lit/Lit), and Ames (df/df) mice (Prop 1 Deficiency). Deficient prostate development in GH inhibitor overexpression animals was previously reported (see Ruan et al, Endocrinology 140:1984-1989, 1999). Analysis of development was determined by dissecting away the periprostatic fat and teasing the glandular structures from the connective tissue in a solution containing collagenase so that the entire glandular tree could be photographed for later structural analysis. Much the same as in the mice overexpressing the mutant growth hormone, the other GH deficient mice had significant impairment of prostate development (p<0.0002) including a reduction in the number of terminal duct tips (TDTs), the area of the prostate gland, the number of quaternary branches and the number of branch points (TABLE 3). Any differences in these GH deficient mice may in part be due to the fact that the different strains were not analyzed at exactly the same age (Lit/Lit 50 days old, Ames 47 days old and bGH transgenic 44 days of age). The n was also different which may have led to greater significance in the Lit/Lit mice.

The fact that GH treatment was capable of restoring impaired prostate development in GH deficient mice was shown in an experiment on Lit/Lit dwarf animals. Groups of animals were treated with either bGH (100 µg over 7 days That IGF-I was also found to be essential for full prostate development was shown in a series of experiments employing IGF-I$^{(-/-)}$ null male mice. They, too, had highly impaired prostate development despite the fact that they had testes that were capable of producing T. The level of serum T in such animals has been found to be 0.6 ng/ml in the knockout mice and 3.3 ng/mL in wild type mice by Baker and colleagues (Baker et al (1996) Mol Endocrinol 10(7):903-918). The highly impaired prostate development was partially but significantly restored when the animals were treated with either des(1-3) IGF-I alone, T alone (silastic capsule) or the combination of T and IGF-I (see Example 1). bGH had no effect on restoring prostate development in these animals incapable of producing their own IGF-I. We, therefore, concluded that the positive effects of bGH that were found to restore prostate development in the growth hormone deficient animals described above occurred entirely through the mediation of IGF-I.

To clearly differentiate between the effects of IGF-I and T on development of the prostate gland, hormone replacement experiments were conducted on IGF-I$^{(-/-)}$ male mice that had been castrated. In addition to evaluating the effect of IGF-I and T on gland structure development described above, we also evaluated the relative effects of these hormones on development of the stromal compartment of the prostate and also on histology of the glandular compartment. This was accomplished by sectioning and staining the prostate to highlight aspects of development.

Castrated IGF-I$^{(-/-)}$ male mice were treated with T (administered by silastic capsules embedded on the backs of animals, subcutaneously). Des (1-3) IGF-I (40 µg/pump) was also implanted subcutaneously. Results of various hormone treatments for 28 days are shown in TABLE 4 and FIG. 5.

TABLE 4

Effect of IGF-I and/or T on prostate development

| | Terminal Duct Tips | Width of TDTs(mm) | Area (cm$^2$) | 4°- branching | Branch Points |
|---|---|---|---|---|---|
| Ventral Prostate | | | | | |
| Control | 14.3 ± 0.3 | 0.116 ± 0.003 | 0.06 ± 0.01 | 6.0 ± 0.0 | 10.3 ± 0.3 |
| IGF-I | 20.3 ± 1.2 [a] | 0.130 ± 0.003 [a] | 0.12 ± 0.01 [a] | 13.3 ± 1.2 [a] | 16.0 ± 1.2 [a] |
| T | 16.3 ± 1.2 | 0.236 ± 0.003 [b] | 0.16 ± 0.01 [a] | 8.0 ± 0.6 [a] | 12.0 ± 1.2 |
| IGF-I + T | 33.3 ± 3.2 [c, d] | 0.350 ± 0.035 [c, e] | 0.55 ± 0.04 [c] | 23.0 ± 0.6 [c] | 31.0 ± 0.9 [c] |
| Dorsal Prostate | | | | | |
| Control | 14.0 ± 0.6 | 0.113 ± 0.003 | 0.07 ± 0.01 | | |
| IGF-I | 16.7 ± 0.3 [a] | 0.130 ± 0.003 [a] | 0.09 ± 0.02 [a] | | |
| T | 17.0 ± 1.2 [a] | 0.227 ± 0.003 [b] | 0.15 ± 0.01 [a] | | |
| IGF-I + T | 24.7 ± 0.3 [c] | 0.410 ± 0.066 [c, e] | 0.49 ± 0.02 [c] | | |

Animal were castrated at 63 days old, hormones were treated two weeks later after castration for 28 days and sacrificed at 105 days.
[a] $P < 0.04$ compared with control.
[b] $P < 0.04$ compared with control and IGF-I.
[c] $P < 0.005$ compared with control, IGF-I or testosterone.
[d] $P < 0.02$ compared with IGF-I.
[e] $P < 0.05$ compared with testosterone.

Figure 5:
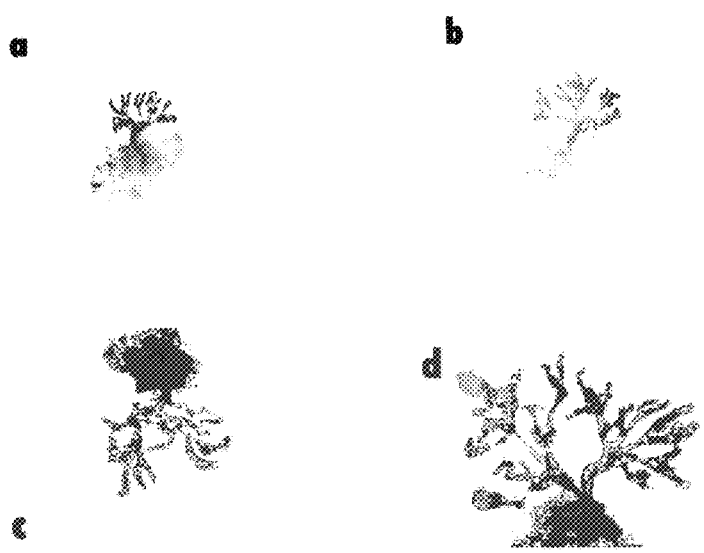
FIG. 5 depicts photomicrographs of ventral prostate glands from castrated IGF-I$^{(-/-)}$ male mice treated for 28 days with either nothing (control (a), IGF-I alone (b), T alone (c) or IGF-I plus T (d).

IGF-I and T acted in synergy on induction of TDTs, width of TDTs, and gland area in both ventral and dorsal prostate development, and on quaternary branching and increasing the number of branch points in the ventral prostate. T had a greater effect on gland area than IGF-I, and IGF-I had a greater effect on quaternary branching and branch points than did T. The relative effects of T and IGF-I will be further differentiated when histological results are considered below. Photomicrographs of representative prostatic trees are shown in FIG. 5.

The relative effects of IGF-I and T on prostate development were also studied in histological sections of whole prostate. This allowed determination of such effects on glandular microstructure and the stromal compartment of the prostate. T had a greater effect on epithelial hyperplasia and lumen size then did IGF-I (see TABLE 5) but IGF-I and T were found to synergize one with the other in each aspect of glandular development. We also found that T alone was capable of stimulating formation of a small amount of probasin in the luminal epithelial cells of the prostate, but that the addition of IGF-I enhanced and increased the formation of probasin (see FIG. 6(i-l) described below) Thus IGF-I was found to synergize with T in gland formation and gland function and differentiation.

Thus, IGF-I has a significantly greater effect on development of the fibromuscular compartment of the prostate than does T. In fact, when T and IGF-I were given together the effect of IGF-I in stimulation of fibromuscular tissue was significantly inhibited. This was true in terms of incorporation of BrdU into fibromuscular cells and in muscle mass as determined by smooth muscle α-actin staining and hematoxylin eosin staining.

Figure 6:
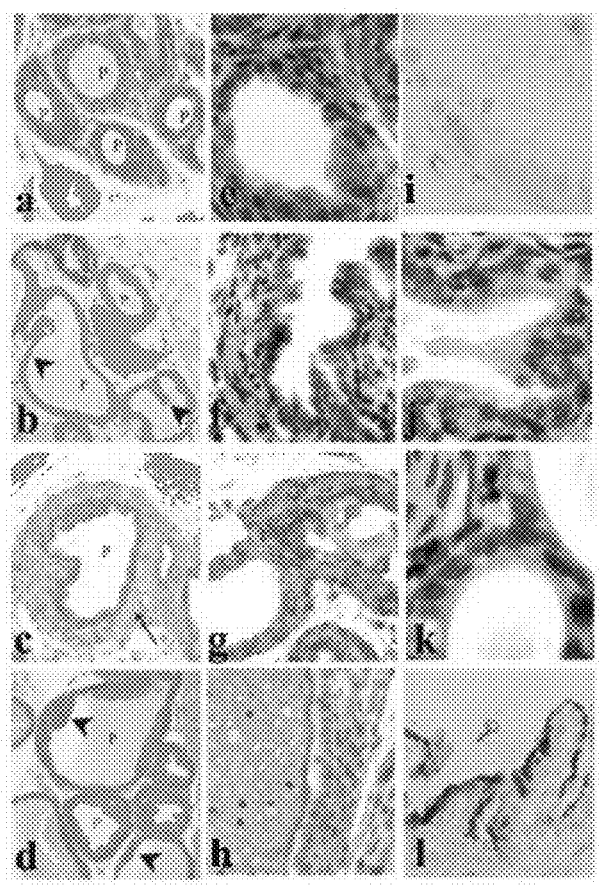
FIG. 6 depicts the effect of IGF-1 and/or T on histological appearance of prostate glands during development. Sections are shown through prostate glands from control animals (a, e, i) and animals treated with T alone (b, f, j), IGF-I alone (c, g, k), and IGF-I plus T (d, h, i). (a-c) show the prostate stained with H-E of the various groups of animals. Arrowheads point to the prostate epithelium. Arrows point to the fibromuscular layer of the prostate obtained from animals treated with IGF-I alone (c). Magnification ×100. (e-h) Smooth muscle-alpha actin immunostaining, brown color, in the fibromuscular layer of the prostate. Magnification ×200. (i-1) Probasin immunostaining, brown color in the epithelial cells of the prostate. Magnification ×400.

FIG. 6 visually demonstrates the differential effects of testosterone and IGF-I alone and in combination on the histological appearance of prostate glands during development. FIG. 6 depicts sections through prostate glands from control animals (FIG. 6(a, e, i)), animals treated with T alone (FIG. 6(b, f, j)), IGF-I alone (FIG. 6(c, g, k)), and IGF-I plus T (FIG. 6(d, h, i)). FIG. 6(a-c) depicts the prostate stained with H-E of the various groups of animals. Arrowheads point to the prostate epithelium. Note the papilar appearance of the prostatic epithelium in the mice treated with T alone (FIG. 6(b)) and a combination of T and IGF-I (FIG. 6(d)). Arrows point to the fibromuscular layer of the prostate obtained from animals treated with IGF-I alone (FIG. 6(c)). Note the marked development of this layer in those animals. FIG. 6(e-h) depicts smooth muscle-alpha actin immunostaining, brown color, in the fibromuscular layer of the

TABLE 5

Effect of IGF-I and/or T on histological structures of the prostate

Mean area of each prostatic component (μm$^2$) and percentage occupied (%)

| | Lumen | Epithelium | Fibromuscular tissue | Mean section size |
|---|---|---|---|---|
| control | 57 × 10$^3$ (33%) | 71 × 10$^3$ (42%) | 43 × 10$^3$ (25%) | 173 × 10$^3$ |
| IGF-I | 288 × 10$^3$ (42%)[a,c] | 78 × 10$^3$ (15%)[b,e] | 236 × 10$^3$ (43%)[a,e] | 543 × 10$^{3a,g}$ |
| T | 369 × 10$^3$ (69%)[a] | 84 × 10$^3$ (15%)[a] | 89 × 10$^3$ (16%)[b] | 543 × 10$^{3a}$ |
| IGF-I + T | 491 × 10$^3$ (70%)[a,d] | 92 × 10$^3$ (13%)[a,f] | 116 × 10$^3$ (16%)[a,f] | 700 × 10$^{3a,f}$ |

Animal were castrated at 56 days old, hormones were given two weeks later after castration for 7 days and sacrificed at 77 days.
[a] $P < 0.0001$ compared with control.
[b] $P < 0.05$ compared with control.
[c] $P < 0.05$ compared with T.
[d] $P < 0.05$ compared with IGF-I or T.
[e] $P < 0.001$ compared with T.
[f] $P < 0.001$ compared with IGF-I or T.
[g] NS compared with T.

prostate. Note the marked development of this layer in the animals treated with IGF-I alone (FIG. 6(g)). FIG. 6(i-l) shows probasin immunostaining, brown color in the epithelial cells of the prostate. Note that only the prostate of those animals treated with a combination of IGF-I and T (I) epithelial cells showed a strong immunostaining. No immunostaining for probasin was detected in the prostatic epithelium of control (FIG. 6(i)) and IGF-I treated animals (FIG. 6(k)). A scattered number of probasin immunopositive epithelial cells were detected in those animals treated with T alone.

Example 4

Inhibitors of IGF-I Action Inhibit Both Glandular and Fibromuscular Development

Assessment of the Effects of IGFBP-1 on Prostate Development Induced by bGH in Castrated Ames Dwarf Mice and on Normal Prostate Development in 4-Wk-Old Intact Wild-Type Mice.

To determine whether IGF-I inhibition could impair prostate development induced by GH-stimulated IGF-I and normal development in eugonadal animals, the effect of IGFBP-1 was tested in the following two models.

Ames Dwarf Mice.

Ames dwarf mice have impaired prostate development because they are deficient in GH. They are also deficient in prolactin, TSH, and gonadotrophins (Andersen et al., 1995, Dev Biol 172:495-503; the entire content of which is incorporated herein by reference). To determine if IGFBP-1 could prevent bGH-induced IGF-I action, 10-wk-old castrated Ames animals were treated with bGH with or without infusion of IGFBP-1 for 7 d. IGFBP-1 inhibited GH-induced fibromuscular and glandular development (Table 6).

at least in part by inhibiting cell division and stimulating apoptosis (Thrasher et al., 1996, J Urol 155:999-1003). Although not wishing to be bound by theory, it is likely that IGFBP-1 acts by competitively inhibiting IGF-I action (Clemmons et al., 1993, Ann NY Acad Sci 692:10-21), but other mechanisms have also been proposed (Van Den Berg et al., 1997, Eur J Cancer 33:1108-1113). Other inhibitors of IGF-I action are predicted to behave similarly.

These findings demonstrate that IGFBP-1 inhibits the normal development of the fibromuscular compartment in eugonadal intact mice and therefore support the likelihood that IGF-I inhibition would be effective in reducing the size of the stromal compartment, even in the absence of supraphysiological concentrations of IGF-I and in the presence of circulating testosterone.

Example 5

Small Molecule IGF-I Receptor Inhibitors Inhibit Both Glandular and Fibromuscular Development To examine further the effect of various compounds on glandular and fibromuscular development of the prostate, somatostatin-14 (SS14, a native somatostatin) and an exemplary small molecule IGF-I receptor inhibitor PQ401 were assessed in a variety of animal models.

In a first experimental approach, the effect of treatment of intact 28 day old male mice with vehicle or PQ401 (a small molecule IGF-I receptor specific inhibitor) or somatostatin-14 (SS14; a native somatostatin) was evaluated. PQ401 and SS14 inhibit IGF-I action. For these experiments, N=5 mice

TABLE 6

Effect of IGFBP-1 on inhibition of GH-induced prostate development in castrated Ames dwarf mice.

|  | Fibromuscular, μm² (×10³) | Epithelium, μm² (×10³) | Lumen, μm² (×10³) | Total, μm² (×10³) |
| --- | --- | --- | --- | --- |
| bGH | 253.4 ± 18.6$^{a,b}$ | 160.5 ± 4.0$^{c,d}$ | 274.7 ± 11.9$^{c,d}$ | 688.6 ± 32.4$^{a,b}$ |
| bGH + BP-1 | 156.9 ± 8.7$^e$ | 145.0 ± 2.9 | 239.1 ± 4.8$^e$ | 540.3 ± 8.9$^e$ |
| Control | 122.6 ± 6.7 | 144.7 ± 3.2 | 188.2 ± 10.4 | 455.5 ± 18.1 |

$^a$P < 0.02 compared with bGH + BP-1.
$^b$P < 0.01 compared with control.
$^c$P < 0.05 compared with bGH + BP-1.
$^d$P < 0.04 compared with control.
$^e$P < 0.04 compared with control.

Figure 7:
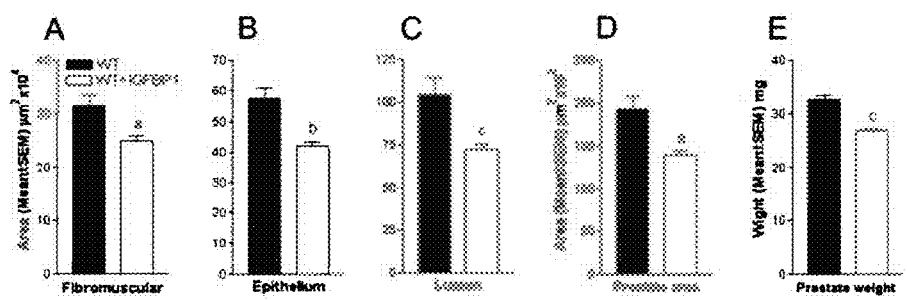
FIG. 7 depicts the effect of IGFBP-1 treatment on prostate structures in intact 28 day old male mice. After 7 d of treatment with IGFBP-1 or vehicle, prostate development in both fibromuscular and glandular compartments was analyzed. Effects on fibromuscular development (A), epithelial development (B), lumen size (C), total prostate area (D), and prostate weight (E) are shown. Effects of IGFBP-1 (compared with control) on cell division and programmed cell death are shown in representative photomicrographs (F) showing the effect of IGFBP-1 (lower row) on cell division (left) and apoptosis (right) compared with control animals (top row) Arrows point to Ki67 or TUNEL staining in stroma, and arrows point to those effects in glands. Magnification, 400×. Effects of Ki67 staining (G) for cell division (left) and effects on programmed cell death by TUNEL (right). WT, Wild type.
Figure 7:
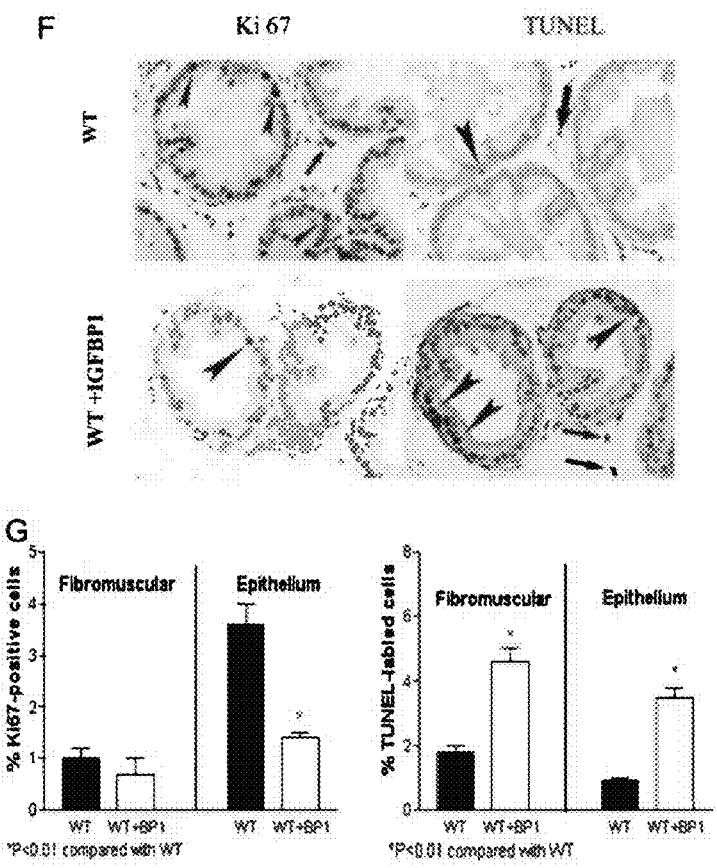

Eugonadal intact mice. The effect of treatment with IGH3P-1 on prostate development in 4-wk-old intact wild-type male mice was also studied. When compared with saline-treated control animals, IGFBP-1 inhibited all fibromuscular development, epithelial development, lumen size, prostate area, and prostate weight (FIG. 7, A-E). IGFBP-1 inhibited cell division in the epithelial compartment, and increased apoptosis in both fibromuscular and epithelial compartments (FIGS. 7, F and G).

These results demonstrate that IGFBP-1 can prevent GH induced fibromuscular and glandular development of the prostate in Ames dwarf male animals, and also inhibit multiple aspects of prostate development in both the fibromuscular and glandular compartments of intact male mice, per group. The results of these experiments are presented below in Tables 7-10:

TABLE 7

| Effect on prostate weight 28 day control: | 26.8 mg ± 1.0 p < 0.0001 compared with other groups |
| --- | --- |
| With PQ401 | 18.4 ± 0.5 (31% reduction) |
| With SS14 | 17 ± 0.7 (37% reduction) |

The results presented Table 7 demonstrate that treatment with either PQ401 or SS14 reduces prostate size in 28 day CD mice to a significant degree.

TABLE 8

Effect on different prostate compartments

| nm² | Animal # | Fibromuscular | epithelial | lumen | total |
|---|---|---|---|---|---|
| 28 days | 2 | 0.234 ± 0.018 | 0.503 ± 0.025 | 0.816 ± 0.096 | 1.55 ± 0.051 |
| 28 D + SS14 | 2 | 0.160 ± 0.014 | 0.445 ± 0.010 | 0.573 ± 0.014 | 1.178 ± 0.017 |
| 28 D + PQ401 | 2 | 0.172 ± 0.009 | 0.652 ± 0.035 | 0.652 ± 0.035 | 1.238 ± 0.053 |

TABLE 9

Effect of treatment on the total area of the circular muscle and the area of the longitudinal muscle by both PQ401 and SS14.

| mm² | 28 day olds controls | 28 Day + SS14 | 28 Day + PQ401 |
|---|---|---|---|
| Circular muscle | 1.322 | 0.438 | 0.789 |
| Longitudinal muscle | 0.939 | 0.486 | 0.868 |

TABLE 10

Effect of PQ401 and SS14 on prostate and body weight

| | 28 D controls | 28 D PQ401 | % Reduction | 28 D SS14 | % Reduction |
|---|---|---|---|---|---|
| Body weight (gm) | 26.9 ± 0.3 | 23.2 ± 0.6 | 14 | 23.9 ± 0.3 | 11 |
| Prostate weight (mg) | 26.8 ± 1.0 | 18.4 ± 0.5 | 31 | 17 ± 0.7 | 37 |

The results depicted in Table 8 (above) demonstrate that both SS14 and PQ401 reduce the size of various compartments of the prostate to a significant degree in this animal model system. The reduction in size of the fibromuscular compartment is particularly noteworthy in light of its role in BPH. Table 9 (above) underscores the ability of SS14 and PQ401 to reduce the size of both the circular and the longitudinal muscles of the prostate. These are the muscle layers which when enlarged cause BPH. Table 10 (above) shows that the reduction in prostate size is enhanced with respect to reduction in overall body weight. In sum, these results show that both SS14 and PQ401 reduce the size (in terms of weight), area, and individual anatomic components of the prostate in mice.

Example 6

Studies in an Animal Model of BPH

Methods:

To evaluate further the efficacy of somatostatin 14 (SS-14) in the treatment of BPH and related urinary tract obstruction, the present inventors used an animal model system in which prostate hyperplasia, together with prostatitis is induced by administration of estradiol to male Wistar rats. The estradiol-treated Wistar rat animal model system was originally described by Robinette (1988, The Prostate 12:271-286; the content of which is incorporated herein in its entirety) as offering an animal model of the inflammation and fibromuscular growth observed in human BPH. Robinette also described the estradiol-treated Wistar rat animal model system as useful for identifying factors and/or xenobiotics that can inhibit or potentially reverse progression of prostatic fibromuscular proliferation. Wilson et al. (Exp Mol Pathol. 2004; 77:7-17; the content of which is incorporated herein in its entirety) also presented guidance pertaining to the estradiol-treated Wistar rat animal model system of Robinette, offering that chronic inflammation induced in the lateral prostate by estrogen treatment is accompanied later by fibromuscular proliferation, which correlates with the prevalence of chronic inflammation in BPH in men. To assay the therapeutic benefit of IGF-I inhibitors in an animal model system, the present inventors utilized the animal model system of Robinette (supra), as modified in accordance with standard methodology as set forth herein.

Three month old Wistar rats were treated for 2 weeks with 1-cm long 0.078 i.d.×0.125 o.d. Silastic tubings filled with estradiol ($E_2$). Another group of estradiol treated animals was also given SS-14 via Alzet pump implanted into the subcutaneous fat of the back, at a dosage of 15 µg/kg/hour. At the end of the treatment period animals were sacrificed and prostates removed en bloc. A total of four animals were analyzed per group.

Prior to fixing and embedding, prostates were weighed. Bladder and coagulating glands were removed and the remaining tissues were embedded with urethral opening down. Blocks were then sectioned at 150 µm intervals.

Results:

In a first set of experiments, the effect of SS14 treatment was assessed in the aforementioned animal model system in which prostate hyperplasia, together with prostatitis is induced by administration of estradiol to Wistar male rats. To stimulate development of prostate hyperplasia, 3 month old intact (eugonadal) male Wistar rats were treated with estradiol ($E_2$) for 2 weeks. It is noteworthy that 3 month old rats are considered to be relatively older rats in the timeline of a rat lifespan, thereby paralleling onset of BPH in older human males. The experimental design of this approach thus serves to create an animal model system that recapitulates numerous features of BPH in a human. In a first set of experiments, SS14 treatment caused a significant reduction in prostate weight of $E_2$-treated rats (p=0.024) as compared to control $E_2$-treated rats (rats treated with vehicle only). Thus, in a model of estrogen induced rat prostatitis and benign prostatic hyperplasia (due to treatment with $E_2$), SS14 reduced prostate weight and gland size.

The results of a second set of experiments are presented in Table 11 below, which depicts the effect of treatment on the whole prostate weight. As shown in Table 11, treatment with SS-14 significantly reduced prostate weight when added to $E_2$ treated rats (p=0.019), demonstrating that it reduces the whole organ bulk.

TABLE 11

Weight (in grams) of prostates of $E_2$- vs. $E_2$ + SS-14-treated rats.

| | $E_2$ | $E_2$ + SS-14 |
|---|---|---|
| Animal #1 | 0.570 | 0.356 |
| Animal #2 | 0.580 | 0.534 |

TABLE 11-continued

Weight (in grams) of prostates of $E_2$- vs. $E_2$ + SS-14-treated rats.

|  | $E_2$ | $E_2$ + SS-14 |
|---|---|---|
| Animal #3 | 0.532 | 0.460 |
| Animal #4 | 0.630 | 0.430 |
| MEAN WEIGHT | 0.578 | 0.445 |

The effect on total area of prostate occupied by glands was also assessed. To determine whether SS-14 would have an inhibitory effect on the glandular component of the prostate, the area of the organ occupied by glands in transverse sections, including the urethra and cut at the level at which the width of the prostate was maximal, was measured. Gland area is expressed as it relates to the total area of the organ in transverse sections. Results are shown below in Table 12. As shown therein, SS-14 significantly reduces the area occupied by glands (p=0.028). This indicates that SS-14 has an independent effect on reducing gland size in this rat model of $E_2$-induced prostate hyperplasia.

TABLE 12

Ratio between the prostate area occupied by glandular elements and the whole organ area in transverse sections.

|  | $E_2$ |  | E2 + SS-14 |
|---|---|---|---|
|  | 0.846661002 |  | 0.84940789 |
|  | 0.857047415 |  | 0.77622466 |
|  | 0.875769946 |  | 0.76274021 |
|  | 0.859580399 |  | 0.81419929 |
| AVERAGE | 0.860 | AVERAGE | 0.801 |
| STDEV | 0.012 | STDEV | 0.039 |
| SEM | 0.006 | SEM | 0.020 |

The effect of SS14 on size of individual glands was also determined. SS-14 also decreased the size of individual glands, although not significantly. The lack of statistical significance, however, may be the result of the limited number of animals examined. In the present studies, the mean gland size was 0.099 mm² in $E_2$-treated rats and 0.078 mm² in animals also given SS-14.

The effect of SS-14 on the Fibromuscular Compartment surrounding the Urethra was also evaluated. To determine whether SS-14 reduced the fibromuscular component of the urethra, tissue sections were immunostained for smooth muscle α actin (αSMA). Each prostate was cut at 5 different levels, with 150 microns between each set of sections. The results of αSMA staining are shown in the photomicrographs depicted in FIG. 8; the whole urethra is indicated by circles and the surrounding fibromuscular layer by arrows. FIG. 8 shows representative sections from one animal treated with $E_2$ (left) vs one treated with $E_2$ SS-14. Treatment with SS-14 strongly reduced the fibromuscular tissue surrounding the urethra (Table 13).

TABLE 13

Area of the fibromuscular component of the urethra in $E_2$ and $E_2$ + SS-14 treated rats.
Fibromuscular Layer Area (mm2)

|  | E2 | E2 + SS14 |
|---|---|---|
| Animal #1 | 1.822 | 2.200 |
| Animal #2 | 2.369 | 1.806 |
| Animal #3 | 4.149 | 1.627 |
| Animal #4 | 3.412 | 2.073 |

TABLE 13-continued

Area of the fibromuscular component of the urethra in $E_2$ and $E_2$ + SS-14 treated rats.
Fibromuscular Layer Area (mm2)

|  | E2 | E2 + SS14 |
|---|---|---|
| MEAN AREA | 2.938 | 1.927 |
| STDEV | 1.043 | 0.258 |
| SEM | 0.521 | 0.129 |

Conclusions

In light of the above, the present inventors have shown that inhibition of IGF-I activity using three different IGF-I inhibitors (IGFBP-1, SS14 and PQ401) inhibits prostate development and growth in a number of animal models: Ames Dwarf animals treated with GH to develop the prostate (Example 4), normal male mice at 28 days of age (treated with IGFBP-1) (Example 4), male mice treated with SS14 or PQ401 (Example 5), and in an animal model of BPH treated with SS-14 (Example 6). These results suggest that IGF-I inhibitors in general will be effective therapeutic agents for patients suffering from BPH.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

We claim:

1. A method for treating a subject with benign prostatic hyperplasia (BPH) disease, the method comprising administering a therapeutically effective amount of an inhibitor of IGF-I activity to a subject with BPH, wherein the inhibitor of IGF-I activity is synthetic somatostatin 14, a somatostatin analog, or a small molecule IGF-I receptor kinase specific inhibitor and the therapeutically effective amount of the inhibitor of IGF-I activity is administered to reduce the amount of prostatic hyperplastic tissue in the subject and thereby alleviate adverse symptoms of BPH in the subject, wherein the adverse symptoms comprise irritative or obstructive voiding pattern, urinary retention, and/or frequent urination with an increased residual urine volume, thereby treating the subject with BPH.

2. The method of claim 1, wherein the somatostatin analog is selected from SOM230, BIM23A779, AN-238, KE108, and RC-121.

3. The method of claim 1, wherein the small molecule IGF-I receptor kinase specific inhibitor is PQ401.

4. The method of claim 1, wherein the therapeutically effective amount of the inhibitor of IGF-I activity is administered via a pharmaceutical composition comprising the therapeutically effective amount of the inhibitor of IGF-I activity and a pharmaceutically acceptable carrier.

5. The method of claim 4, wherein the pharmaceutical composition consists essentially of the therapeutically effective amount of an inhibitor of IGF-I activity.

6. The method of claim 1, wherein the subject is a human.

7. A method for treating a subject with symptoms comprising irritative or obstructive voiding pattern, urinary retention, and/or frequent urination with an increased residual urine volume, said symptoms resulting from fibromuscular and glandular hyperplasia of the prostate, the method comprising administering a therapeutically effective amount of an inhibitor of IGF-I activity to the subject, wherein the inhibitor of IGF-I activity is synthetic somatostatin 14, a somatostatin analog, or a small molecule IGF-I receptor kinase specific inhibitor and the therapeutically effective amount of the inhibitor of IGF-I activity is administered to provide symptomatic relief for the subject, thereby treating the subject with symptoms comprising irritative or obstructive voiding pattern, urinary retention, and/or frequent urination with an increased residual urine volume.

8. The method of claim 7, wherein the somatostatin analog is selected from SOM230, BIM23A779, AN-238, KE108, and RC-121.

9. The method of claim 7, wherein the small molecule IGF-I receptor kinase specific inhibitor is PQ401.

10. The method of claim 7, wherein the therapeutically effective amount of the inhibitor of IGF-I activity is administered via a pharmaceutical composition comprising the therapeutically effective amount of the inhibitor of IGF-I activity and a pharmaceutically acceptable carrier.

11. The method of claim 10, wherein the pharmaceutical composition consists essentially of the therapeutically effective amount of an inhibitor of IGF-I activity.

12. The method of claim 7, wherein the subject is a male human.

13. A method for treating benign prostatic hyperplasia (BPH) disease in a patient to delay a need for surgical treatment of the patient with BPH, the method comprising administering a therapeutically effective amount of an inhibitor of IGF-I activity to the patient with BPH, wherein the inhibitor of IGF-I activity is synthetic somatostatin 14, a somatostatin analog or a small molecule IGF-I receptor kinase specific inhibitor and the therapeutically effective amount of the inhibitor of IGF-I activity is administered to reduce the amount of prostatic hyperplastic tissue in the patient and thereby delay the need for surgical treatment to reduce the amount of prostatic hyperplastic tissue in the patient.

14. A method for reducing an amount of prostatic hyperplastic tissue in a subject with benign prostatic hyperplasia (BPH) disease, the method comprising administering a therapeutically effective amount of an inhibitor of IGF-I activity to a subject with BPH, wherein the inhibitor of IGF-I activity is synthetic somatostatin 14, a somatostatin analog, or a small molecule IGF-I receptor kinase specific inhibitor and the therapeutically effective amount of the inhibitor of IGF-I activity is administered to reduce the amount of prostatic hyperplastic tissue in the subject and thereby alleviate adverse symptoms of BPH in the subject, wherein the adverse symptoms comprise irritative or obstructive voiding pattern, urinary retention, and/or frequent urination with an increased residual urine volume, thereby treating the subject with BPH.

15. A method for reducing fibromuscular and glandular hyperplasia of the prostate in a subject, the method comprising administering a therapeutically effective amount of an inhibitor of IGF-I activity to the subject, wherein the inhibitor of IGF-I activity is synthetic somatostatin 14, a somatostatin analog, or a small molecule IGF-I receptor kinase specific inhibitor and the therapeutically effective amount of the inhibitor of IGF-I activity reduces the fibromuscular and glandular hyperplasia of the prostate in the subject.

* * * * *